United States Patent
Acosta et al.

(10) Patent No.: US 8,083,788 B2
(45) Date of Patent: *Dec. 27, 2011

(54) APPARATUS AND METHODS FOR POSITIONING PROSTHESES FOR DEPLOYMENT FROM A CATHETER

(75) Inventors: Pablo Acosta, Newark, CA (US); Bernard Andreas, Redwood City, CA (US); Stephen Kao, Sunnyvale, CA (US); Joe Karratt, Millbrae, CA (US); Steve Landreville, Mountain View, CA (US); Eric Lang, Foster City, CA (US); David Sanderson, Burlingame, CA (US); Craig Welk, Tracy, CA (US); David W. Snow, Menlo Park, CA (US)

(73) Assignee: Xtent, Inc., Menlo Park, CA (US)

( * ) Notice: Subject to any disclaimer, the term of this patent is extended or adjusted under 35 U.S.C. 154(b) by 1358 days.

This patent is subject to a terminal disclaimer.

(21) Appl. No.: 11/563,793

(22) Filed: Nov. 28, 2006

(65) Prior Publication Data
US 2007/0100423 A1    May 3, 2007

Related U.S. Application Data

(63) Continuation of application No. 10/884,616, filed on Jul. 2, 2004, now Pat. No. 7,182,779, which is a continuation-in-part of application No. 10/874,859, filed on Jun. 22, 2004, now abandoned, which is a continuation-in-part of application No. 10/637,713, filed on Aug. 8, 2003, now Pat. No. 7,309,350, which is a continuation-in-part of application No. 10/412,714, filed on Apr. 10, 2003, now Pat. No. 7,137,993, which is a continuation-in-part of application No. 10/306,813, filed on Nov. 27, 2002, now abandoned.

(60) Provisional application No. 60/364,389, filed on Mar. 13, 2002, provisional application No. 60/336,967, filed on Dec. 3, 2001.

(51) Int. Cl.
*A61F 2/06* (2006.01)
(52) U.S. Cl. ...................................................... 623/1.11
(58) Field of Classification Search ................ 623/1.11, 623/1.12; 606/191–198
See application file for complete search history.

(56) References Cited

U.S. PATENT DOCUMENTS
4,069,825 A    1/1978    Akiyama
(Continued)

FOREIGN PATENT DOCUMENTS
DE    1 953 1659    3/1997
(Continued)

OTHER PUBLICATIONS

Office Action of Japanese Patent Application No. 2007-519284, mailed Oct. 26, 2010, 6 pages total [English Translation Included].
(Continued)

*Primary Examiner* — Kevin T Troung
(74) *Attorney, Agent, or Firm* — Kilpatrick Townsend and Stockton LLP

(57) ABSTRACT

Apparatus for delivering stents to body lumens include a flexible catheter shaft, an expandable member, a tubular prosthesis selectively movable in an axial direction over the expandable member, and a stop member disposed on the catheter shaft near the distal end of the catheter shaft for stopping the prosthesis at a deployment position on the expandable member. A variety of different stop members are provided according to various embodiments, such as stop members disposed outside the expandable member, stop members disposed inside the expandable member, movable stop members, and the like. Methods of delivering stents are also provided.

59 Claims, 27 Drawing Sheets

U.S. PATENT DOCUMENTS

| | | |
|---|---|---|
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,391,172 A | 2/1995 | Williams et al. |
| 5,421,955 A | 6/1995 | Lau et al. |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,531,735 A | 7/1996 | Thompson |
| 5,534,007 A * | 7/1996 | St. Germain et al. ........ 623/1.11 |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A | 1/1997 | Martinez et al. |
| 5,607,444 A | 3/1997 | Lam |
| 5,607,463 A | 3/1997 | Schwartz et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A * | 11/1997 | Yurek et al. ................. 623/1.11 |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,997,563 A | 12/1999 | Kretzers et al. |
| 6,004,328 A | 12/1999 | Solar |
| 6,007,517 A | 12/1999 | Anderson |
| 6,022,359 A | 2/2000 | Frantzen |
| 6,022,374 A | 2/2000 | Imran |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duerig |
| 6,183,509 B1 | 2/2001 | Dibie |
| 6,187,034 B1 | 2/2001 | Frantzen |

| Patent No. | Date | Inventor(s) |
|---|---|---|
| 6,190,402 B1 | 2/2001 | Horton et al. |
| 6,196,995 B1 | 3/2001 | Fagan |
| 6,200,337 B1 | 3/2001 | Moriuchi et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 * | 10/2002 | Stack et al. ............ 623/1.11 |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 * | 12/2003 | Dusbabek et al. ............ 623/1.11 |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,778,316 B2 | 8/2004 | Halas et al. |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,913,619 B2 | 7/2005 | Brown et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,175,654 B2 | 2/2007 | Bonsignore et al. |
| 7,182,779 B2 * | 2/2007 | Acosta et al. ............ 623/1.11 |
| 7,192,440 B2 | 3/2007 | Andreas et al. |
| 7,220,755 B2 | 5/2007 | Betts et al. |
| 7,238,197 B2 | 7/2007 | Sequin et al. |
| 7,241,308 B2 | 7/2007 | Andreas et al. |
| 7,244,336 B2 | 7/2007 | Andreas et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,534,449 B2 | 5/2009 | Saltzman et al. |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0037358 A1 | 3/2002 | Barry et al. |
| 2002/0052642 A1 | 5/2002 | Cox et al. |
| 2002/0091439 A1 | 7/2002 | Baker et al. |

| | | |
|---|---|---|
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0093061 A1 | 5/2004 | Acosta et al. |
| 2004/0093067 A1 | 5/2004 | Israel |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0125051 A1 | 6/2005 | Eidenschink et al. |
| 2005/0131008 A1 | 6/2005 | Betts et al. |
| 2005/0143827 A1 | 6/2005 | Globerman et al. |
| 2005/0165378 A1 | 7/2005 | Heinrich et al. |
| 2005/0209674 A1 | 9/2005 | Kutscher et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0149863 A1 | 6/2009 | Andreas et al. |
| 2009/0234428 A1 | 9/2009 | Snow et al. |
| 2009/0264979 A1 | 10/2009 | Kao et al. |
| 2010/0004729 A1 | 1/2010 | Chew et al. |

FOREIGN PATENT DOCUMENTS

| | | |
|---|---|---|
| DE | 1 963 0469 | 1/1998 |
| DE | 199 50 756 | 8/2000 |
| DE | 101 03 000 | 8/2002 |
| EP | 0 282 143 | 9/1988 |
| EP | 0 505 686 | 9/1992 |
| EP | 0 714 640 | 6/1996 |
| EP | 0 596 145 | 5/1997 |
| EP | 1 290 987 A2 | 3/2003 |
| EP | 1 318 765 | 6/2003 |
| JP | 03-133446 | 6/1991 |
| JP | 10-503663 | 4/1998 |
| JP | 10-295823 | 11/1998 |
| JP | 2935561 B2 | 8/1999 |
| JP | 2001-190687 | 7/2001 |
| JP | 2004-121343 A | 4/2004 |
| WO | WO 95/26695 A2 | 10/1995 |
| WO | WO 96/39077 | 12/1996 |
| WO | WO 99/01087 | 1/1999 |
| WO | WO 00/12832 A3 | 3/2000 |
| WO | WO 00/15151 | 3/2000 |
| WO | WO 00/32136 | 6/2000 |

| | | |
|---|---|---|
| WO | WO 00/56237 | 9/2000 |
| WO | WO 00/72780 | 12/2000 |
| WO | WO 01/91918 | 12/2001 |
| WO | WO 02/085253 | 10/2002 |
| WO | WO 02/098326 | 12/2002 |
| WO | WO 03/022178 | 3/2003 |
| WO | WO 03/051425 | 6/2003 |
| WO | WO 2004/043299 A1 | 5/2004 |
| WO | WO 2004/052237 A2 | 6/2004 |
| WO | WO 2005/009295 | 2/2005 |
| WO | WO 2007/053187 | 5/2007 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13, XP00976354.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

* cited by examiner

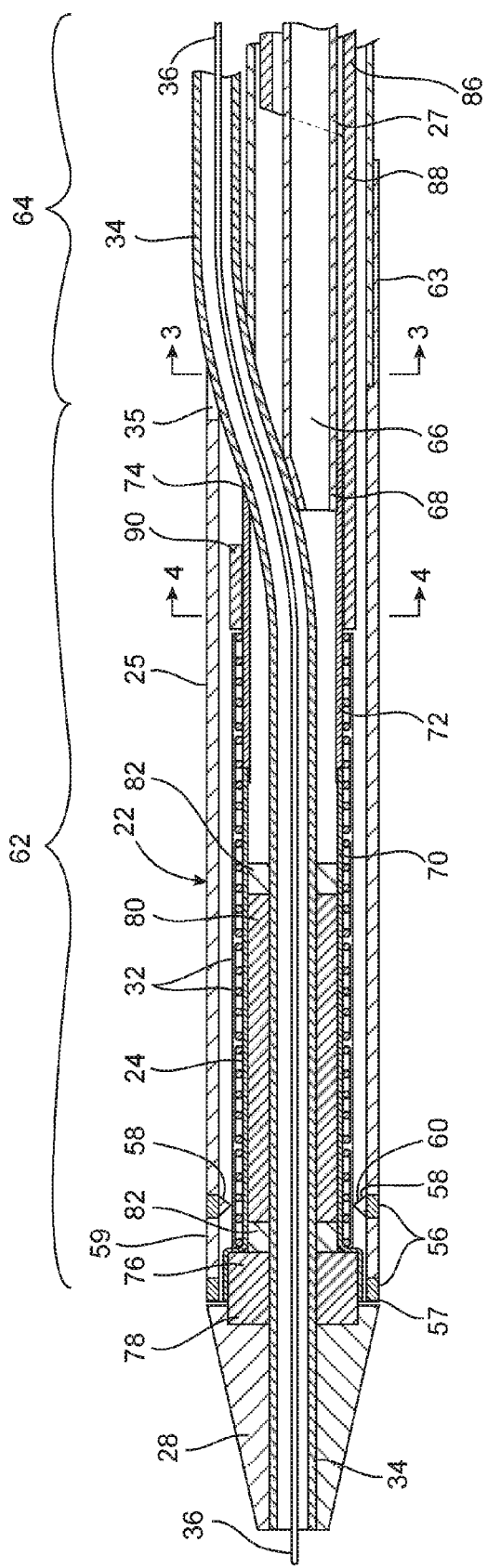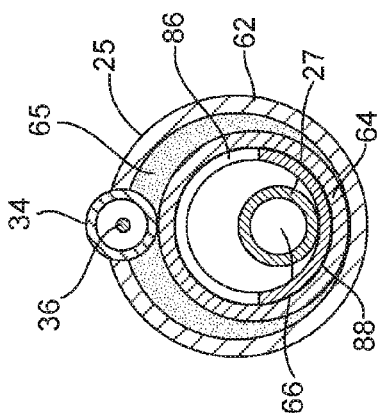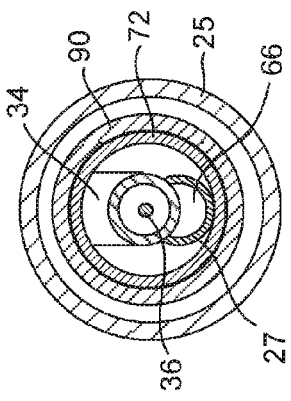

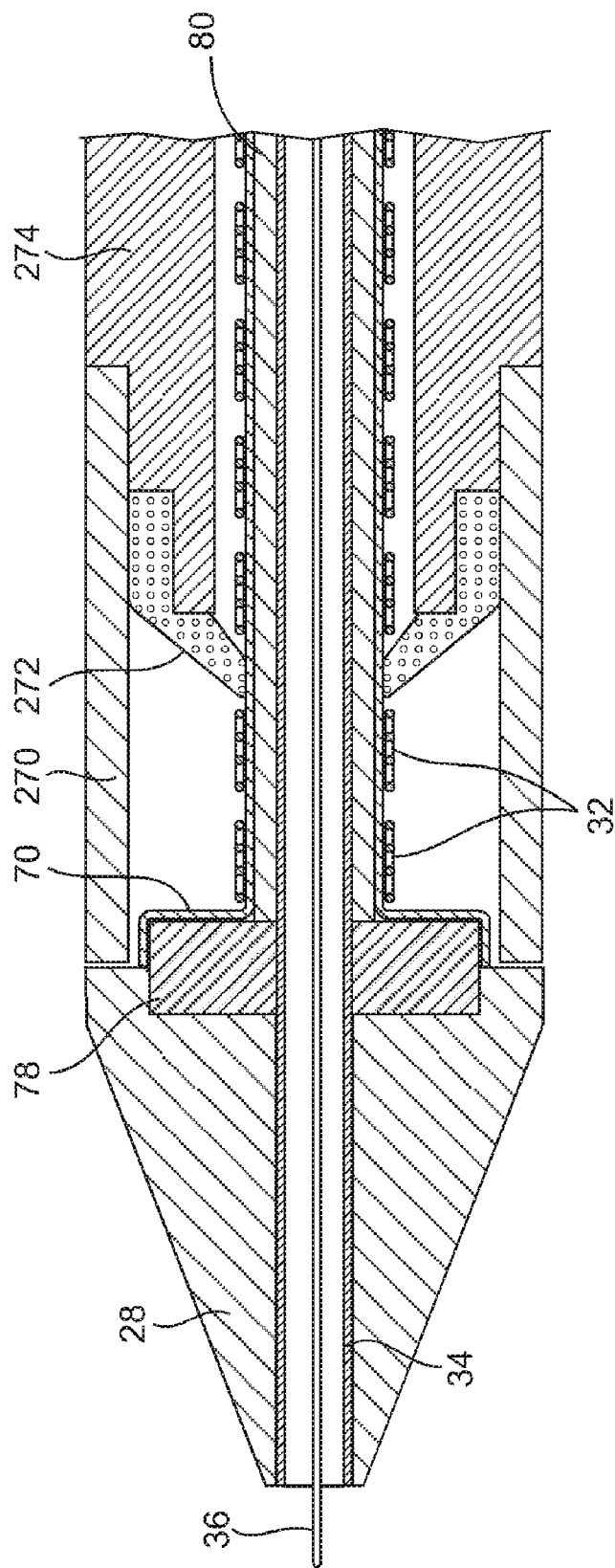
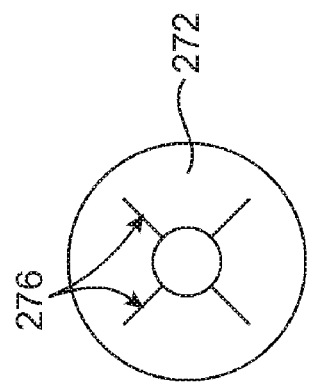
FIG. 2C
FIG. 2D

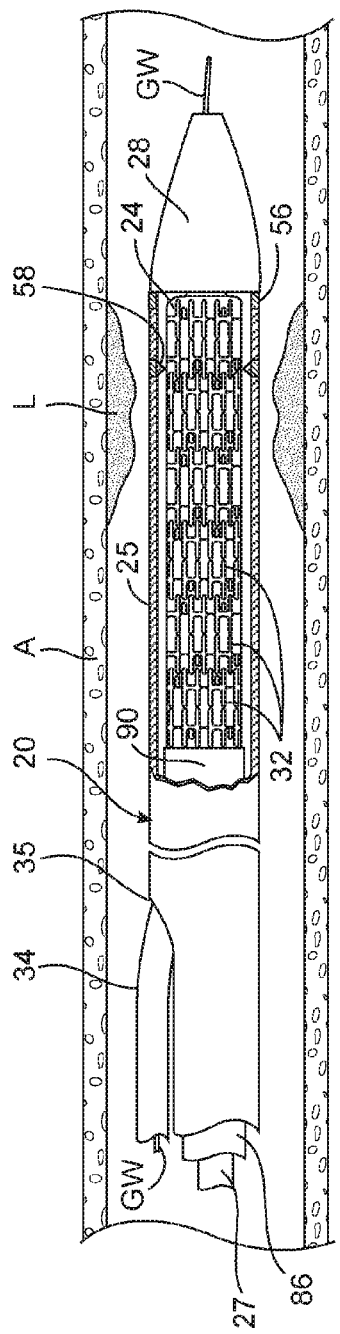
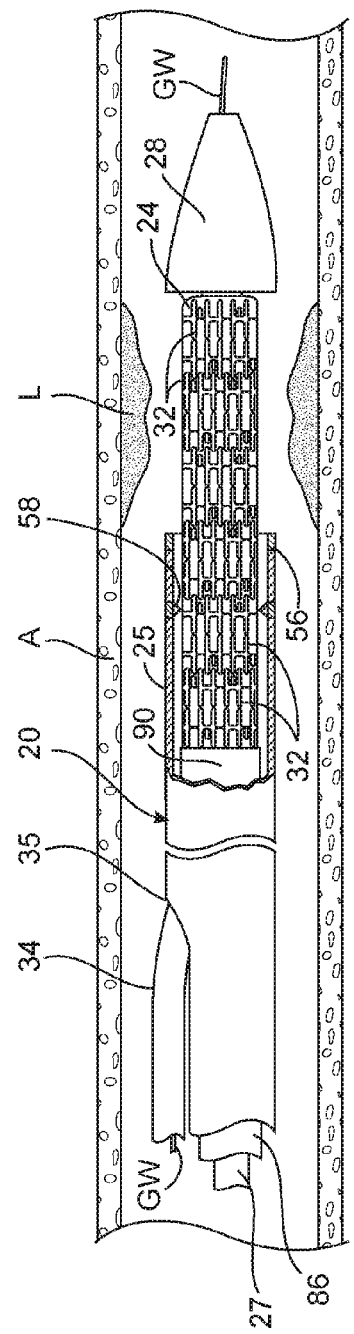
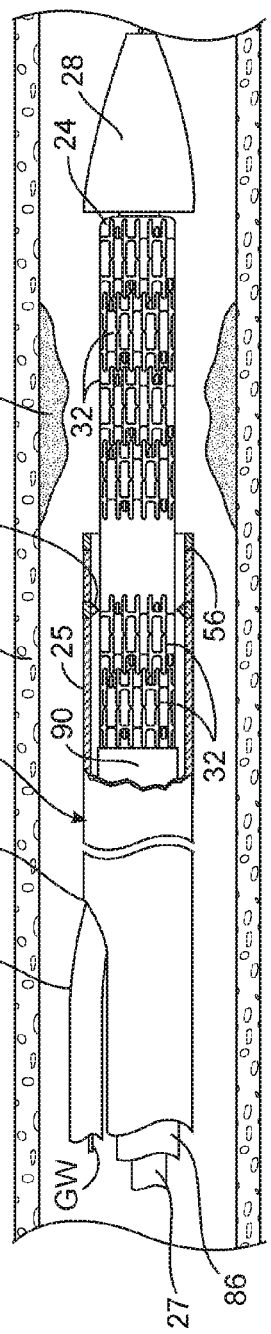
FIG. 7A
FIG. 7B
FIG. 7C

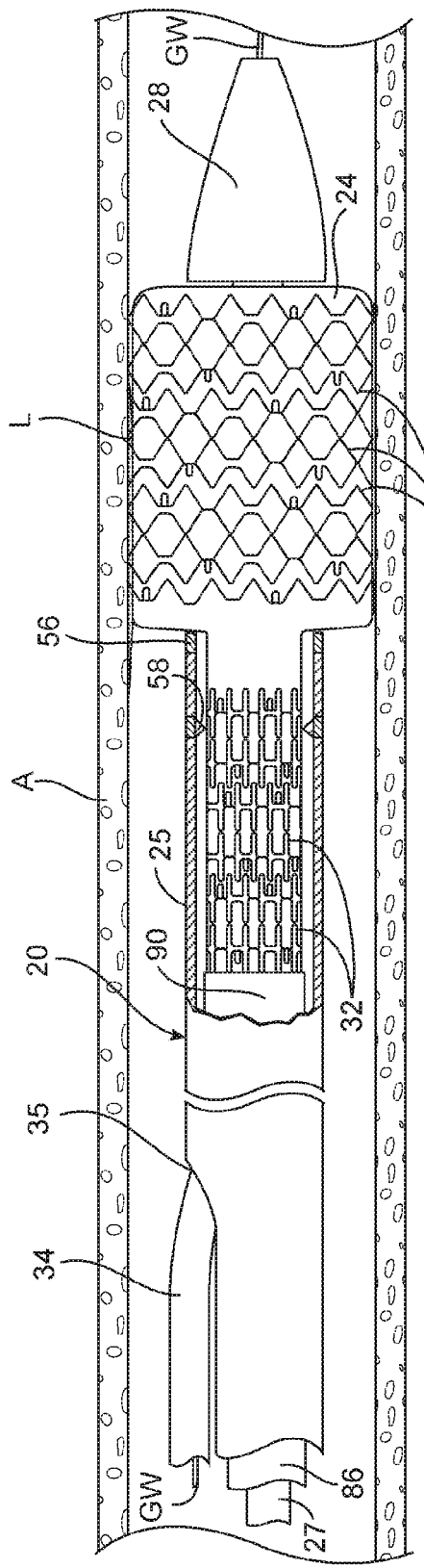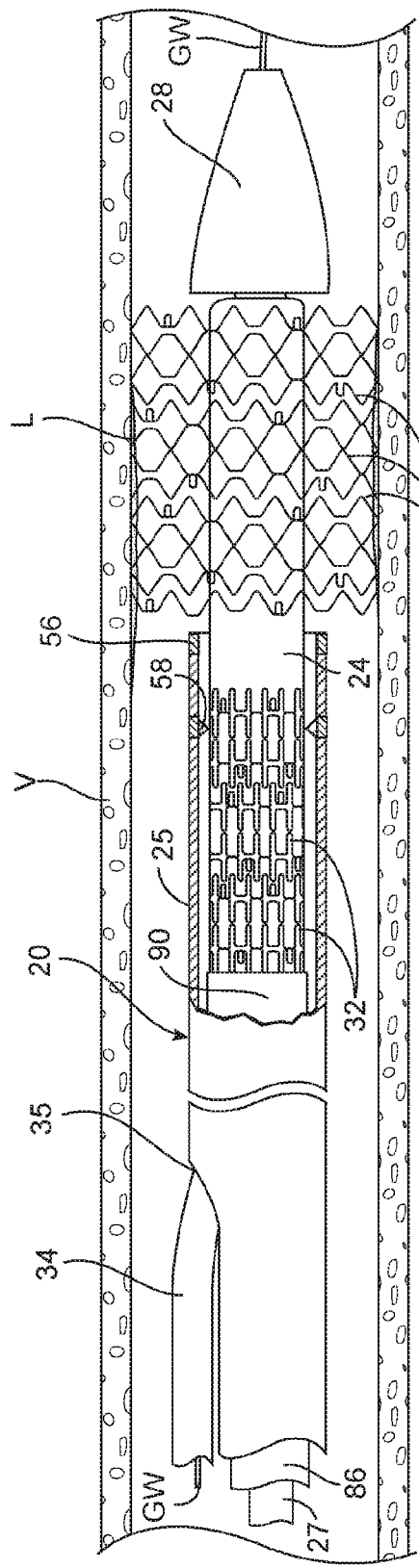

APPARATUS AND METHODS FOR POSITIONING PROSTHESES FOR DEPLOYMENT FROM A CATHETER

CROSS-REFERENCES TO RELATED APPLICATIONS

This application is a continuation of U.S. application Ser. No. 10/884,616, filed Jul. 2, 2004, which is a continuation-in-part of application Ser. No. 10/874,859, filed Jun. 22, 2004, which is a continuation-in-part of co-pending application Ser. No. 10/637,713, filed Aug. 8, 2003, which is a continuation-in-part of application Ser. No. 10/412,714, filed Apr. 10, 2003, which is a continuation-in-part of application Ser. No. 10/306,813, filed Nov. 27, 2002, which is a non-provisional of provisional application Ser. No. 60/336,967, filed Dec. 3, 2001, and a non-provisional of provisional application Ser. No. 60/364,389, filed Mar. 13, 2002, the disclosures of which are incorporated herein by reference.

BACKGROUND OF THE INVENTION

Field of the Invention

This invention relates generally to vascular catheters, and more specifically to stents and stent delivery catheters for deployment in the coronary arteries and other vessels.

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. However, in recent years, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters typically inserted through a femoral artery. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed.

Current stent delivery technology, however, suffers from a number of drawbacks. For example, current stent delivery catheters are not capable of customizing the length of the stent in situ to match the size of the lesion to be treated. While lesion size may be measured prior to stenting using angiography or fluoroscopy, such measurements may be inexact. If a stent is introduced that is found to be of inappropriate size, the delivery catheter and stent must be removed from the patient and replaced with a different device of correct size.

Moreover, current stent delivery devices cannot treat multiple lesions with a single catheter. Current devices are capable of delivering only a single stent with a single catheter, and if multiple lesions are to be treated, a new catheter and stent must be introduced for each lesion to be treated.

Further, current stent delivery devices are not well-adapted for treating vascular lesions that are very long and/or in curved regions of a vessel. Current stents have a discrete length that is relatively short due to their stiffness. If current stents were made longer so as to treat longer lesions, they would not conform well to the curvature of vessels or to the movement of vessels on the surface of the beating heart. On the other hand, any attempt to place multiple stents end-to-end in longer lesions is hampered by the inability to maintain appropriate inter-stent spacing and to prevent overlap of adjacent stents.

Additionally, some stent delivery catheters and angioplasty balloon catheters, particularly those having movable external sheaths to enclose the stent or balloon, suffer from poor tracking and cumbersome interaction with guidewires. Some such catheters utilize an "over-the-wire" design in which the guidewire extends through an inner lumen of the catheter from its proximal end to its distal end, a design that makes catheter exchanges cumbersome and time-consuming. Rapid exchange designs have also been proposed for such catheters wherein the guidewire extends through the distal end of the catheter and out through a port in a sidewall of the sheath. However, in these designs the guidewire inhibits smooth retraction of the sheath and, if the sheath is retracted a substantial distance, the port can become so displaced from the distal end of the catheter that the guidewire does not slide smoothly as the catheter is moved.

In some stent delivery catheters, stents are mounted on an expandable balloon member, and the balloon is inflated to expand the stents. Currently available catheters, however, do not typically provide for positioning stents on a balloon in situ. If a stent is advanced over a balloon on a catheter positioned in a vessel, it is often difficult or impossible to determine how far the stent should be advanced relative to the balloon. A stent may be advanced too far, pushing it off the distal end of the balloon, so that all or a portion of the stent does not expand properly with balloon expansion. At other times, a stent may not be advanced far enough along the balloon, in which case the balloon portion not covered by stent material (known as "balloon overhang") may dilate the vessel when expanded, potentially causing trauma to the vessel.

Finally, many stent delivery catheters suffer from inflexibility and high cross-sectional profile, which hamper endovascular positioning.

For these and other reasons, stents and stent delivery catheters are needed which enable the customization of stent length in situ, and the treatment of multiple lesions of various sizes, without requiring removal of the delivery catheter from the patient. Such stents and stent delivery catheters should be capable of treating lesions of particularly long length and lesions in curved regions of a vessel, and should be highly flexible to conform to vessel shape and movement. Such stent delivery catheters should further be of minimal cross-sectional profile and should be highly flexible for endovascular positioning through tortuous vascular pathways. Ideally, such stent delivery catheters would also allow for accurate and repeatable positioning of one or more stents in a desired position for deployment from the catheter in situ. At least some of these objectives will be met by the present invention.

BRIEF SUMMARY OF THE INVENTION

The invention provides apparatus and methods for delivering prostheses or stents into body lumens. In one aspect of the present invention, apparatus for delivering a prosthesis into a target vessel includes: a flexible catheter shaft having a proximal end and a distal end; an expandable member coupled with the catheter shaft near the distal end movable from a contracted configuration to an expanded configuration; a tubular prosthesis selectively movable in an axial direction over the expandable member; and a stop member disposed on the catheter shaft near the distal end for stopping the prosthesis at a deployment position on the expandable member.

In some embodiments, the stop member has a first shape when the expandable member is in the contracted configuration and a second shape when the expandable member is in the expanded configuration. In one embodiment, the stop member is resiliently biased into the first shape, whereby the stop member recoils from the second shape to the first shape when the expandable member contracts from the expanded configuration to the contracted configuration. Alternatively, the stop member may be movable relative to the expandable member from a first position when the expandable member is in the contracted configuration to a second position when the expandable member is in the expanded configuration. Optionally, such a stop member may be resiliently biased into the first position, whereby the stop member recoils from the second position to the first position when the expandable member contracts from the expanded configuration to the contracted configuration. Also optionally, the apparatus may further include an actuator for selectively moving the stop member between the first and second positions.

In some embodiments, the expandable member of the apparatus has a deployment portion and a tapered portion tapering distally from the deployment portion, the stop member being adapted to stop the tubular prosthesis on the deployment portion proximal to the tapered portion. In one embodiment, the tapered portion is everted within the deployment portion in the contracted configuration. Optionally, the expandable member may have a proximal end mounted at a first mounting point on the catheter shaft and a distal end mounted at a second mounting point that is movable relative to the first mounting point. In such an embodiment, the first mounting point and the second mounting point may be interconnected by a shaft, the shaft having an elongatable section which elongates upon expansion of the expandable member.

In some embodiments, the apparatus further includes a pusher slidably disposed over the catheter shaft and engaging the tubular prosthesis for positioning the tubular prosthesis over the expandable member. Optionally, the apparatus may further comprise a sheath slidably disposed over the catheter shaft and the tubular prosthesis and being axially movable relative thereto. In some embodiments, the prosthesis self-expands to a shape suitable for engaging the target vessel when the sheath is refracted to expose the prosthesis. In some embodiments, the sheath is axially positionable relative to the expandable member and configured to restrain expansion of a selected portion of the expandable member. Optionally, the sheath may be reinforced to prevent expansion thereof by the expandable member. In some embodiments, the tubular prosthesis comprises a plurality of prosthesis segments. In such embodiments, the sheath may be axially movable relative to the prosthesis segments and configured to restrain expansion of a selectable number of prosthesis segments.

In some embodiments, the stop member is external to the expandable member. Alternatively, the stop member may reside within the expandable member, be fixed to the expandable member and/or the like. In one embodiment, the stop member comprises a sleeve having a proximal portion disposed over a distal end of the expandable member. For example, in one embodiment, the sleeve has a compressible portion, wherein expanding the expandable member compresses the compressible portion thereby moving the proximal portion relative to the expandable member. In other embodiments, the stop member comprises a cone shaped member disposed over a tapered distal end of the expandable member. Optionally, the cone-shaped member may be movable between a contracted shape and an expanded shape upon expansion of the expandable member. In other embodiments, the stop member comprises a tubular member disposed distally of the expandable member. In some embodiments, a distal end of the expandable member is everted such that when the expandable member is inflated the everted portion becomes a tapered portion. Optionally, the distal end of the expandable member may be coupled to an elongatable shaft such that expanding the expandable member elongates the shaft.

In yet another embodiment, the stop member comprises a cone shaped member coupled with the catheter shaft inside the expandable member. Alternatively, the stop member may include a movable distal nose cone slidably disposed over the distal end of the catheter shaft from a first position over a distal end of the expandable member to a second position distal to the distal end of the expandable member and an inner shaft slidably coupled to the catheter shaft and attached to the nose cone. In another embodiment, the apparatus further includes a nosecone disposed distally of the expandable member, and the stop member comprises a sleeve extending proximally from the nose cone to cover a distal end of the expandable member. Such a sleeve may optionally be biased, such as with a flexible bend, to dispose a proximal end of the sleeve within a sheath of the apparatus, to thus avoid the proximal end of the sleeve from catching on the distal end of the sheath.

In alternative embodiments, the at least one stop member comprises one or more surface features on a distal portion of the expandable member. In some embodiments, for example, the surface features may include but are not limited to bumps, ridges, spines, ribs, scales, pleats and wings. In another embodiment, the surface feature comprises a thickened distal portion of the expandable member, the thickened distal portion including a proximal abutment. In other embodiments, the surface features comprise at least one material selected from the group consisting of Dacron, C-flex, high friction materials, gels and adhesives.

In another aspect of the present invention, an apparatus for delivering a prosthesis into a target vessel includes: a flexible catheter shaft having a proximal end and a distal end; a plurality of tubular prostheses slidably disposed over the catheter shaft; a sheath disposed over the catheter shaft and the tubular prostheses and being axially movable relative thereto; and a stop member coupled with the catheter shaft near the distal end for stopping at least one of the tubular prostheses at a deployment position along the catheter shaft. In some embodiments, the apparatus further includes a pusher axially movable relative to the catheter shaft and being in engagement with at least one tubular prosthesis for positioning the tubular prosthesis over the expandable member. In some embodiments, the tubular prostheses self-expand upon being exposed out of the sheath.

The apparatus may optionally include an expandable member coupled with the catheter shaft near the distal end movable from a contracted configuration to an expanded configuration. In one embodiment, the stop member has a first shape when the expandable member is in the contracted configuration and a second shape when the expandable member is in the expanded configuration. Optionally, the stop member may be resiliently biased into the first shape, whereby the stop member recoils from the second shape to the first shape when the expandable member contracts from the expanded configuration to the contracted configuration. In some embodiments, the stop member is movable relative to the expandable member from a first position when the expandable member is in the contracted configuration to a second position when the expandable member is in the expanded configuration.

Optionally, the stop member may be resiliently biased into the first position, whereby the stop member recoils from the second position to the first position when the expandable member contracts from the expanded configuration to the contracted configuration. In some embodiments, the apparatus further includes an actuator for selectively moving the stop member between the first and second positions.

In one embodiment, the expandable member has a deployment portion and a tapered portion tapering distally from the deployment portion, the stop member being adapted to stop the tubular prosthesis on the deployment portion proximal to the tapered portion. In one embodiment, the tapered portion is everted within the deployment portion in the contracted configuration. The expandable member may have a proximal end mounted at a first mounting point on the catheter shaft and a distal end mounted at a second mounting point that is movable relative to the first mounting point. In one embodiment, the first mounting point and the second mounting point are interconnected by a shaft, the shaft having an elongatable section which elongates upon expansion of the expandable member.

In various embodiments, the stop member of the apparatus may have any or a plurality of the features and configurations described above.

In another aspect of the invention, an apparatus for delivering a prosthesis into a target vessel comprises: a flexible catheter shaft having a proximal end, a distal end and at least one lumen; an expandable member coupled with the catheter shaft near the distal end, the expandable member having a deployment portion and a tapered portion tapering distally from the deployment portion; a tubular prosthesis axially slidable over the expandable member; and a sheath slidably disposed over the expandable member and the tubular prosthesis and being axially movable relative thereto, an actuator for moving the expandable member a set distance relative to the sheath from a retracted position in which the tubular prosthesis is over the tapered portion to an extended position in which the tubular prosthesis is disposed over the deployment portion.

In some embodiments, the actuator is disposed on a handle at the proximal end of the catheter shaft for advancing the expandable member by the set distance. In some embodiments, the actuator comprises a compressible spring member associated with an element selected from the sheath, the catheter shaft, or the expandable member, wherein retracting the expandable member compresses the spring member and releasing the expandable member causes the spring member to recoil, thus moving the expandable member by the set distance.

In yet another aspect of the present invention, a method of delivering a prosthesis in a target vessel of a patient involves: advancing a tubular prosthesis along a delivery catheter; stopping the prosthesis at a deployment location on the delivery catheter with a stop member thereon; and expanding at least part of the tubular prosthesis into engagement with the target vessel. In a preferred embodiment, the tubular prosthesis comprises a plurality of prosthesis segments, and advancing the tubular prosthesis comprises positioning a first selected number of the prosthesis segments on an expandable member of the delivery catheter for expansion therewith. Some embodiments further involve positioning a sheath of the delivery catheter to expose the first selected number of prosthesis segments and to constrain expansion of a second selected number of the prosthesis segments. Optionally, such embodiments may further involve covering a proximal portion of the expandable member by the sheath to constrain the proximal portion from expansion while a distal portion of the expandable member expands. Alternatively, expanding at least part of the tubular prosthesis may involve exposing the first selected number of prosthesis segments by positioning the sheath, to allow the first selected number of segments to self-expand.

In some embodiments, advancing the tubular prosthesis comprises pushing the prosthesis using a pusher of the delivery catheter. Stopping the tubular prosthesis with the stop member may involve abutting the distal end of the prosthesis against the stop member. Alternatively, stopping the tubular prosthesis with the stop member may comprise advancing a distal end portion over the stop member to frictionally engage the prosthesis.

In some embodiments, expanding the tubular prosthesis comprises expanding an expandable member on the delivery catheter. In one embodiment, the stop member expands with the expandable member. Optionally, the stop member may move from a first position to a second position as the expandable member expands. The method may further involve retracting the expandable member after the tubular prosthesis is expanded, wherein the expandable member recoils to the first position when the expandable member is contracted. In some embodiments, the method also involves moving the stop member from a first position to a second position relative to the expandable member after stopping the tubular prosthesis.

In another aspect of the invention, a method of delivering a prosthesis in a target vessel of a patient comprises: advancing a plurality of prostheses along a delivery catheter; stopping a first selected number of the prostheses at a deployment location on the delivery catheter with a stop member thereon; and expanding the first selected number of prostheses into engagement with the target vessel. In some embodiments, advancing the tubular prosthesis comprises positioning the first selected number of the prostheses on an expandable member for expansion therewith. Optionally, the method may also include positioning a sheath of the delivery catheter to expose the first selected number of prostheses and to constrain expansion of a second selected number of the prostheses. In some embodiments, the method further includes covering a proximal portion of the expandable member by the sheath to constrain the proximal portion from expansion while a distal portion of the expandable member expands. In some embodiments, the first selected number of tubular prostheses self-expand when the sheath is retracted.

In some embodiments, the tubular prostheses are self-expanding, and the method further includes positioning a sheath of the delivery catheter to expose the first selected number of prosthesis segments and to constrain expansion of a second selected number of the prosthesis segments. The method may further involve, after the expanding step: advancing a second selected number of prostheses along the delivery catheter; stopping the second selected number of prostheses with the stop member; and expanding the second selected number of prostheses into engagement with the target vessel. In some embodiments, the first and second selected number of prostheses are expanded by expanding an expandable member of the delivery catheter. Alternatively, the first and second selected number of prostheses may be self-expanding. In some embodiments, advancing the tubular prosthesis comprises pushing the prosthesis using a pusher of the delivery catheter.

In some embodiments, expanding the first selected number of prostheses comprises expanding an expandable member on the delivery catheter. In some embodiments, the stop member expands with the expandable member. In some embodiments, the stop member moves from a first position to a second position as the expandable member expands. The method may optionally further include retracting the expandable member after the tubular prosthesis is expanded, wherein the expandable member recoils to the first position when the expandable member is contracted. In some embodiments, the method involves moving the stop member from a first position to a second position relative to the expandable member after stopping the tubular prosthesis.

Further aspects of the nature and advantages of the invention will become apparent from the detailed description below taken in conjunction with the drawings.

BRIEF DESCRIPTION OF THE DRAWINGS

FIG. 2A is a side cross-section of a distal portion of the stent delivery catheter of FIG. 1 with expandable member deflated and sheath advanced distally.

FIG. 2C is a side cross-section of a distal portion of a stent delivery catheter according to an embodiment of the invention.

FIG. 2D is an end-on view of a stent valve member included in the stent delivery catheter of FIG. 2C.

FIG. 3 is a transverse cross-section through line 3-3 of FIG. 2A.

FIG. 4 is a transverse cross-section through line 4-4 of FIG. 2A.

FIGS. 7A-7E are side cut-away views of the stent delivery catheter of the invention positioned in a vessel with the stent segments of FIGS. 5A-5B, illustrating various steps of delivering a prosthesis according to the method of the invention.

DETAILED DESCRIPTION OF THE INVENTION

Figure 1:
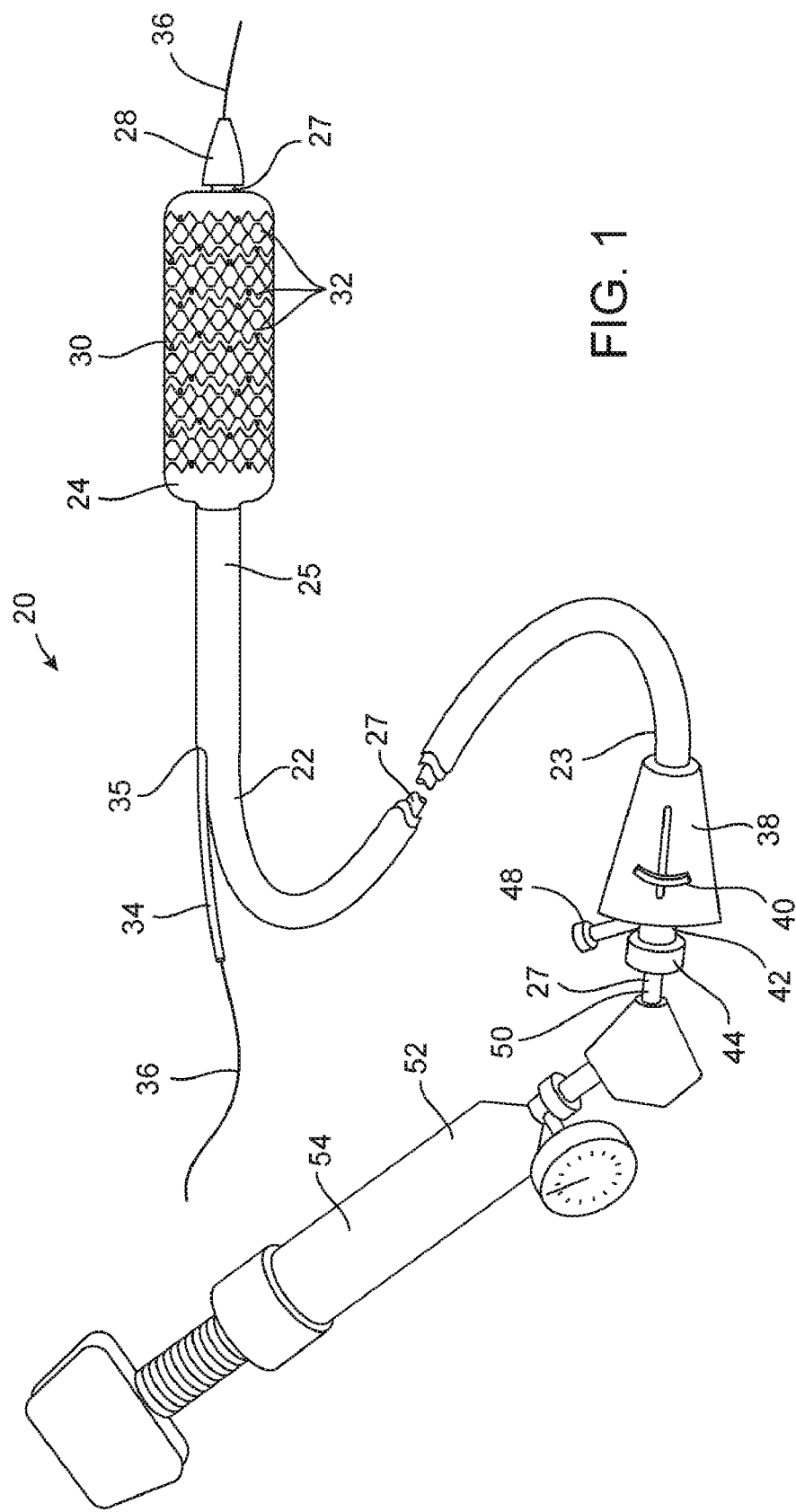
FIG. 1 is a perspective view of a stent delivery catheter according to the invention with sheath retracted and expandable member inflated.

A first embodiment of a stent delivery catheter according to present invention is illustrated in FIG. 1. Stent delivery catheter 20 includes a catheter body 22 comprising an outer sheath 25 slidably disposed over an inner shaft 27. An expandable member 24, preferably an inflatable balloon (shown in an inflated configuration), is mounted to inner shaft 27 and is exposed by retracting sheath 25 relative to inner shaft 27. A tapered nosecone 28, composed of a soft elastomeric material to reduce trauma to the vessel during advancement of the device, is mounted distally of expandable member 38. A stent 30, which preferably comprises a plurality of separate or separable stent segments 32, is disposed on expandable member 24 for expansion therewith. A guidewire tube 34 is slidably positioned through a guidewire tube exit port 35 in sheath 25 proximal to expandable member 24. A guidewire 36 is positioned slidably through guidewire tube 34, expandable member 24, and nosecone 28 and extends distally thereof.

A handle 38 is mounted to a proximal end 23 of sheath 25 and includes an actuator 40 slidably mounted thereto for purposes described below. An adaptor 42 is mounted to the proximal end of handle 38 and provides a catheter port 44 through which inner shaft 27 is slidably positioned. A flush port 48 is mounted to the side of adaptor 42 through which a fluid such as saline can be introduced into the interior of catheter body 22. An annular seal (not shown) in catheter port 44 seals around inner shaft 27 to prevent fluid from leaking through catheter port 44. Optionally, a clamp (not shown) such as a threaded collar, can be mounted to catheter port 44 to lock inner shaft 27 relative to handle 38.

Inner shaft 27 has a proximal end 50 to which is mounted an inflation adaptor 52. Inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. Inflation adaptor 52 is in fluid communication with expandable member 24 via an inflation lumen (described below) in inner shaft 27 to enable inflation of expandable member 24.

In alternative embodiments, handle 38 may have any of a number of suitable configurations and features, such as those described in U.S. patent application Ser. Nos. 10/746,466, filed Dec. 23, 2003, and 10/814,593, filed Mar. 3, 2004, which are both fully incorporated herein by reference.

Referring now to FIGS. 2A, 2B, 3 and 4, which show a distal portion of the stent delivery catheter in cross-section, sheath 25 may be extended up to nosecone 28 to fully surround expandable member 24 and stent segments 32. One or more radiopaque markers 56 are mounted near a distal end 57 of sheath 25 to facilitate visualization of the position of sheath 25 using fluoroscopy. In a preferred embodiment, two annular markers 56 are spaced apart a length equal to the length of one of stent segments 32 for purposes described more fully below. Sheath 25 further includes a valve member 58 preferably spaced proximally from distal end 57 a distance equal to the length of one of stent segments 32. Valve member 58 has an inwardly extending flange 60 configured to frictionally engage stent segments 32 and thereby restrict the sliding movement of stent segments 32 distally relative to sheath 25. Flange 60 may be a polymeric material integrally formed with sheath 25 or a separate annular member bonded or otherwise mounted to sheath 25. Various embodiments of valve member 58 are described in co-pending U.S. patent application Ser. No. 10/412,714, filed Apr. 10, 2003, which is fully incorporated herein by reference.

Sheath 25 has a distal extremity 62 configured to surround expandable member 24 and stent segments 32 disposed thereon when in an unexpanded configuration. Distal extremity 62 extends proximally to a junction 63, preferably aligned with the location of guidewire tube exit port 35, where distal extremity 62 is joined to a proximal extremity 64 that extends proximally to handle 38 (see FIG. 1). In a preferred embodiment, distal extremity 62 has a length of about 15-35 cm and proximal extremity 64 as a length of about 100-125 cm. Proximal extremity 64 may be constructed of a variety of biocompatible polymers or metals, preferably being stainless steel or Nitinol. Distal extremity 62 may be a polymer such as PTFE, FEP, polyimide, or Pebax, and is preferably reinforced with a metallic or polymeric braid to resist radial expansion when expandable member 24 is expanded.

In some embodiments, distal extremity 62 includes a distal-most portion 59, which extends beyond stent valve 58 distally to the distal end of sheath 25. In some embodiments, distal-most portion 59 and the rest of distal extremity 62 are made of the same material or combination of materials and may even comprise a unitary piece or extrusion. In other embodiments, distal-most portion 59 may include different material(s) than those used for making the rest of distal extremity 62. In some embodiments, distal-most portion 59 is made of a relatively stiff material so that if a stent segment 32 is positioned therein distally of stent valve 58, distal-most portion 59 will prevent segment 32 from being deployed when expandable member 24 is expanded. In some embodiments, for example, distal-most portion 59 may comprise a metal ring or hypotube or a polymer with an embedded or attached metal braid, ribs or other reinforcement.

Referring to FIGS. 2C and 2D, an alternative embodiment of a distal end of a catheter device is shown. In this embodiment, a sheath 274 has a distal-most portion 270 of a stiff material such as a metal hypotube or polymer with metal braid mounted to the exterior of sheath 274. Sandwiched between distal most portion 270 and sheath 274 is a tubular, tapered, flexible stent valve 272, which again facilitates separation and deployment of stent segments 32. Flexible stent valve 272 has a central opening 273 through which stent segments 32 may be advanced by applying distal force to pusher 86 (described below). Flexible stent valve 272 is adapted to dilate, stretch and/or deflect radially outwardly when engaged by a stent segment 32, then resiliently return to a non-dilated shape to engage the next stent segment 32 in line. Flexible stent valve 272 may be made of any suitable elastomeric material, such as a medical grade urethane. In some embodiments, as shown in end-on view in FIG. 2D, flexible stent valve 272 may include one or more slits 276 to enhance flexibility and facilitate passage of stent segments 32 therethrough.

Preferably, proximal extremity 64 has a smaller transverse dimension than distal extremity 62 to accommodate the added width of guidewire tube 34 within the vessel lumen, as well as to maximize flexibility and minimize profile. In one embodiment, shown in FIG. 3, distal extremity 62 is a tubular member having a first outer diameter, preferably about 1.0-1.5 mm, and proximal extremity 64 is a tubular member having a second, smaller outer diameter, preferably about 0.7-1.0 mm. At the junction of proximal extremity 64 with distal extremity 62, a proximally-facing crescent-shaped opening 65 is formed between the two tubular members that creates guidewire tube exit port 35. Excess space within crescent-shaped opening 65 may be filled with a filler material such as adhesive.

In an alternative embodiment (not shown), a hole is formed in the sidewall of distal extremity 62 or proximal extremity 64 to create guidewire tube exit port 35. Proximally of guidewire tube exit port 35, the wall of sheath 25 adjacent to guidewire tube 34 is flattened or collapsible inwardly thereby reducing the transverse dimension of sheath 25 to accommodate the width of guidewire tube 34.

Guidewire tube 34 is slidably positioned through guidewire tube exit port 35. Preferably, guidewire tube exit port 35 is configured to provide a total or partial fluid seal around the periphery of guidewire tube 34 to limit blood flow into the interior of sheath 25 and to limit leakage of saline (or other flushing fluid) out of sheath 25. This may be accomplished by sizing guidewire tube exit port 35 appropriately so as to form a fairly tight frictional seal around guidewire tube 34 while still allowing the sliding motion thereof relative to sheath 25. Alternatively an annular sealing ring may be mounted in guidewire tube exit port 35 to provide the desired seal.

Guidewire tube exit port 35 will be positioned to provide optimal tracking of stent delivery catheter 20 through the vasculature and maximizing the ease with which the catheter can be inserted onto and removed from a guidewire to facilitate catheter exchanges. Usually, guidewire tube exit port 35 will be positioned at a location proximal to expandable member 24 when sheath 25 is extended fully distally up to nosecone 28, but a distance of no more than one-half the length of sheath 25 from distal end 57. In preferred embodiments for coronary applications, guidewire tube exit port 35 is spaced proximally a distance of about 20-35 cm from the distal end 57 of sheath 25.

Guidewire tube 34 should extend proximally from guidewire tube exit port 35 a distance at least as long as the longest possible stent that may be deployed, e.g. 30-200 mm, to allow for retraction of sheath 25 that distance while retaining a portion of guidewire tube 34 external to sheath 25. Preferably guidewire tube 34 extends proximally a distance of about 3-15 cm from guidewire tube exit port 35 when sheath 25 is in a fully distal position, with the proximal end thereof disposed a distance of about 23-50 cm from the distal tip of nosecone 28. Where stent delivery catheter 20 is to be positioned through a guiding catheter, the proximal end of guidewire tube 34 will preferably be positioned so as to be within the guiding catheter when expandable member 24 is positioned at the target site for stent deployment. Guidewire tube 34 is preferably a highly flexible polymer such as PTFE, FEP, polyimide, or Pebax, and may optionally have a metal or polymer braid embedded in it to increase kink-resistance.

Inner shaft 27 forms an inflation lumen 66 that is in communication with interior of expandable member 24. In the distal extremity of stent delivery catheter 20 inner shaft 27 is preferably formed of a polymer such as PTFE, FEP, polyimide, or Pebax, and may be reinforced with a metallic braid for added radial strength and kink resistance. In the proximal extremity of delivery catheter 20, inner shaft 27 may be a similar polymer or a metal such as stainless steel or Nitinol.

Expandable member 24 has an expandable balloon member 70 that is joined to a non-expandable tubular leg 72. Expandable balloon member 70 is a semi-compliant polymer such as Pebax or Nylon. Tubular leg 72 is preferably a polymer such as polyimide, PTFE, FEP or Pebax and may optionally be reinforced with a metal or polymer braid. Tubular leg 72 has an open proximal end 74 through which guidewire tube 34 extends. Proximal end 74 of tubular leg 72 is fixed to distal end 68 of inner shaft 27 and to guidewire tube 34, forming a fluid-tight seal. Balloon member 70 has a distal end 76 bonded to an annular stop 78, which is mounted to nosecone 28. Stop 78 has a size and shape selected to engage stent segment 32 and provide a stop against which stent segments 32 can be located in the ideal deployment position without being pushed beyond the distal end of balloon member 70. This embodiment of stop 78, as well as a number of other embodiments, are described more fully below with reference to FIGS. 9-19. Guidewire tube 34 passes through the interior of balloon member 70 and is mounted to nosecone 28, thereby providing a passage through the distal portion of catheter body 22 through which guidewire 36 may pass.

Optionally, within the interior of balloon member 70 an annular base member 80 is mounted to guidewire tube 34 and has a diameter selected to urge balloon member 70 against stent segments 32 in their unexpanded configuration, thereby providing frictional engagement with stent segments 32. This helps to limit unintended sliding movement of stent segments 32 on balloon member 70. Base member 80 may be made of a soft elastomer, foam, or other compressible material. Adjacent to the distal and proximal ends of base member 80 two annular radiopaque markers 82 are mounted to guidewire tube 34, facilitating visualization of the location of balloon member 70 with fluoroscopy and enabling appropriate positioning of stent segments 32 on balloon member 70. Alternatively, only a single marker 82 at the distal end of base member 80 may be used, or markers may be placed at other locations on nosecone 28, guidewire tube 34, or inner shaft 27. Such markers may be made of various radiopaque materials such as platinum/iridium, tantalum, and other materials.

Stent segments 32 are slidably positioned over balloon member 70. Depending upon the number of stent segments 32 loaded in stent delivery catheter 20, stent segments 32 may be positioned over both balloon member 70 and tubular leg 72. In an exemplary embodiment, each stent segment is about 2-8 mm in length, and up to 10-50 stent segments may be positioned end-to-end in a line over balloon member 70 and tubular leg 72. Stent segments 32 preferably are in direct contact with each other, but alternatively separate spacing elements may be disposed between adjacent stent segments, the spacing elements being movable with the stent segments along balloon member 70. Such spacing elements may be plastically deformable or self-expanding so as to be deployable with stent segments 32 into the vessel, but alternatively could be configured to remain on balloon member 70 following stent deployment; for example, such spacing elements could comprise elastic rings which elastically expand with balloon member 70 and resiliently return to their unexpanded shape when balloon member 70 is deflated. The spacing elements could be pushed to the distal end of balloon member 70 against stop 78 as additional stent segments 32 are advanced distally.

Stent segments 32 are preferably a malleable metal so as to be plastically deformable by expandable member 24 as they are expanded to the desired diameter in the vessel. Alternatively, stent segments 32 may be formed of an elastic or super elastic shape memory material such as Nitinol so as to self-expand upon release into the vessel by retraction of sheath 25. Stent segments 32 may also be composed of polymers or other suitable biocompatible materials, including biodegradable polymers, metals, salts, ceramics, and proteins. In embodiments including self-expanding stent segments 32, expandable member 24 may be used for predilatation of a lesion prior to stent deployment and/or for augmenting the expansion of the self-expanding stent segments 32. Predilatation methods and devices are described, for example, in U.S. patent application Ser. No. 10/794,405, filed Mar. 3, 2004, which is fully incorporated herein by reference.

In preferred embodiments, stent segments 32 are coated with a drug that inhibits restenosis, such as Rapamycin, Paclitaxel, analogs, prodrugs, or derivatives of the foregoing, or other suitable agent, preferably carried in a durable or bioerodable polymeric carrier. Alternatively, stent segments 32 may be coated with other types of drugs and therapeutic materials such as antibiotics, thrombolytics, anti-thrombotics, anti-inflammatories, cytotoxic agents, anti-proliferative agents, vasodilators, gene therapy agents, radioactive agents, immunosuppressants, and chemotherapeutics. Such materials may be coated over all or a portion of the surface of stent segments 32, or stent segments 32 may include apertures, pores, holes, channels, or other features in which such materials may be deposited.

Stent segments 32 may have a variety of configurations, including those described in copending application Ser. No. 10/738,666, filed Dec. 16, 2003, which is fully incorporated herein by reference. Other preferred stent configurations are described below. Stent segments 32 are preferably completely separate from one another without any interconnections, but alternatively may have couplings between two or more adjacent segments which permit flexion between the segments. As a further alternative, one or more adjacent stent segments may be connected by separable or frangible couplings that are separated prior to or upon deployment, as described in copending application Ser. No. 10/306,813, filed Nov. 27, 2002, which is incorporated herein by reference.

Figure 2B:
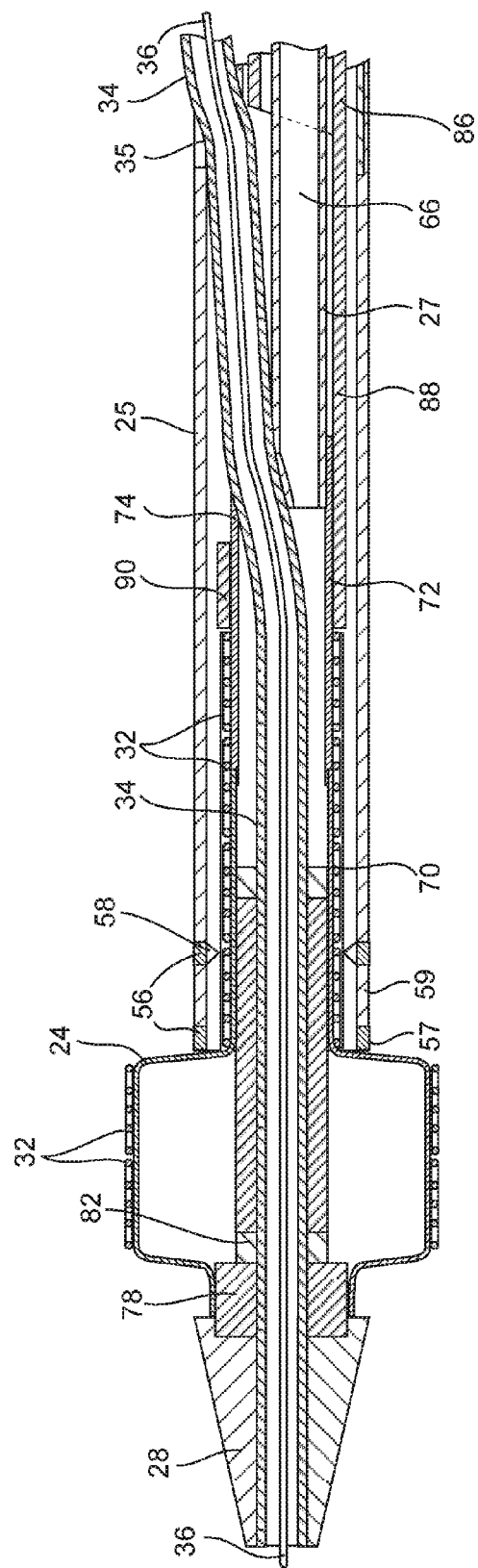
FIG. 2B is a side cross-section of a distal portion of the stent delivery catheter of FIG. 1 with expandable member inflated and sheath retracted.

A pusher tube 86 is slidably disposed over inner shaft 27 and has a distal extension 88 coupled to a pusher ring 90. Pusher ring 90 is slidable over tubular leg 72 and engages the stent segment 32 at the proximal end of the line of stent segments 32. At its proximal end (not shown), pusher tube 86 is coupled to sliding actuator 40 on handle 38 (see FIG. 1). In this way pusher tube 86 can be advanced distally relative to inner shaft 27 to urge stent segments 32 distally over expandable member 24 (or pusher tube 86 may be held in position while retracting expandable member 24 relative to stent segments 32) until the stent segments engage stop 78. In addition, pusher tube 86 can be used to hold stent segments 32 in place on expandable member 24 while sheath 25 is retracted to expose a desired number of stent segments 32, as shown in FIG. 2B. Pusher tube 86 may be constructed of a variety of biocompatible polymers or metals, preferably being stainless steel or Nitinol. Distal extension 88 and pusher ring 90 may be a polymer such as PTFE, FEP, polyimide, or Pebax, and are preferably reinforced with a metallic or polymeric braid to resist radial expansion when expandable member 24 is expanded.

With sheath 25 retracted a desired distance, expandable member 24 is allowed to expand when inflation fluid is delivered through inflation lumen 66, thereby expanding a desired number of stent segments 32 exposed distally of sheath 25. The remaining portion of expandable member 24 and the remaining stent segments 32 within sheath 25 are constrained from expansion by sheath 25.

FIG. 2B further illustrates that when sheath 25 is retracted relative to expandable member 24, guidewire tube exit port 35 becomes further away from the point at which guidewire 36 exits the proximal end 74 of tubular leg 72, increasing the distance that guidewire 36 must pass within the interior of sheath 25. Advantageously, guidewire tube 34 provides a smooth and continuous passage from the tubular leg 72 through guidewire tube exit port 35, eliminating any problems that might result from changing the alignment of the two. This is particularly important in the present invention where the stent delivery catheter may carry a large number of stent segments 32 and sheath 25 may be retracted a substantial distance relative to expandable member 24, resulting in substantial misalignment of guidewire tube exit port 35 relative to tubular leg 72.

Figure 5A:
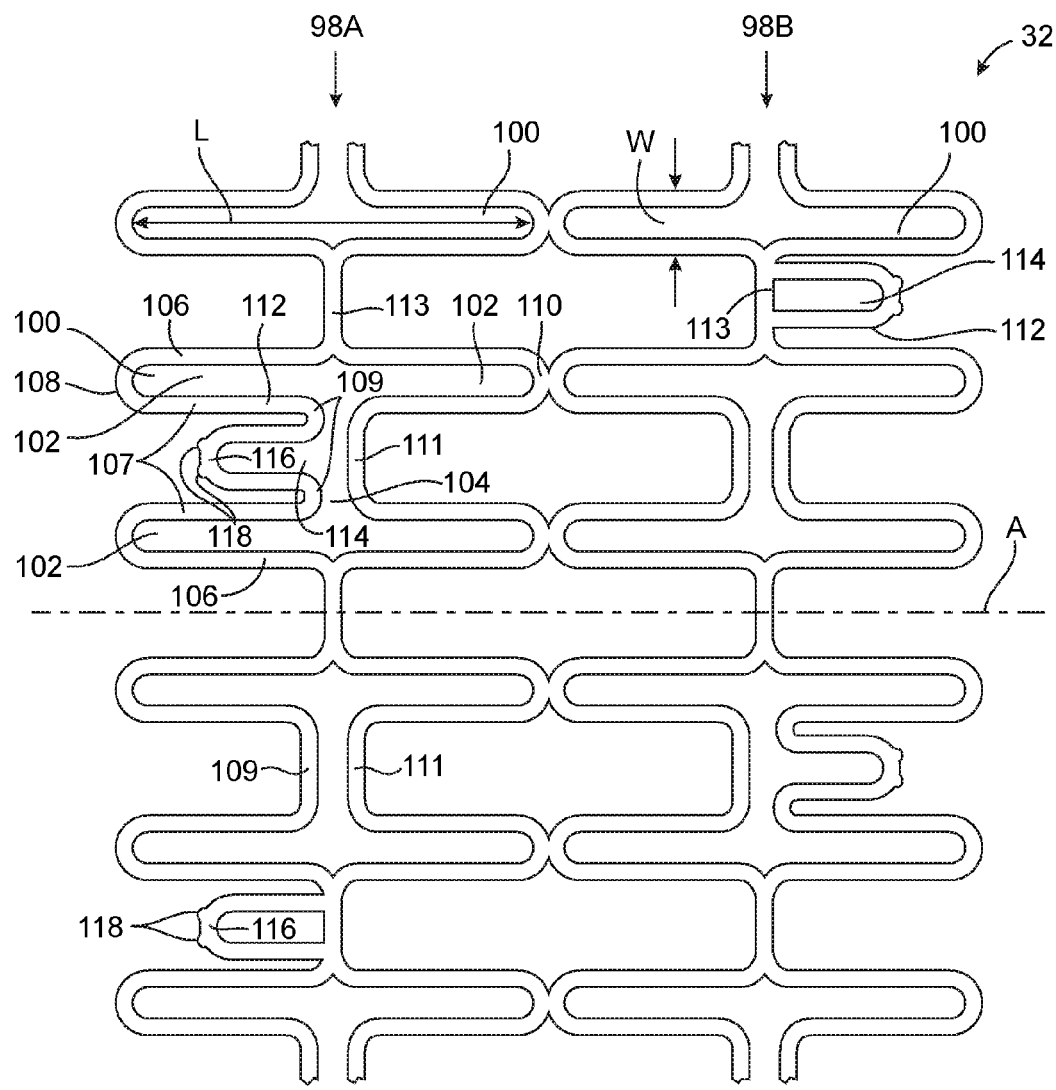
FIG. 5A is a side view of a first embodiment of a stent segment according to the invention in an unexpanded configuration.
Figure 5B:
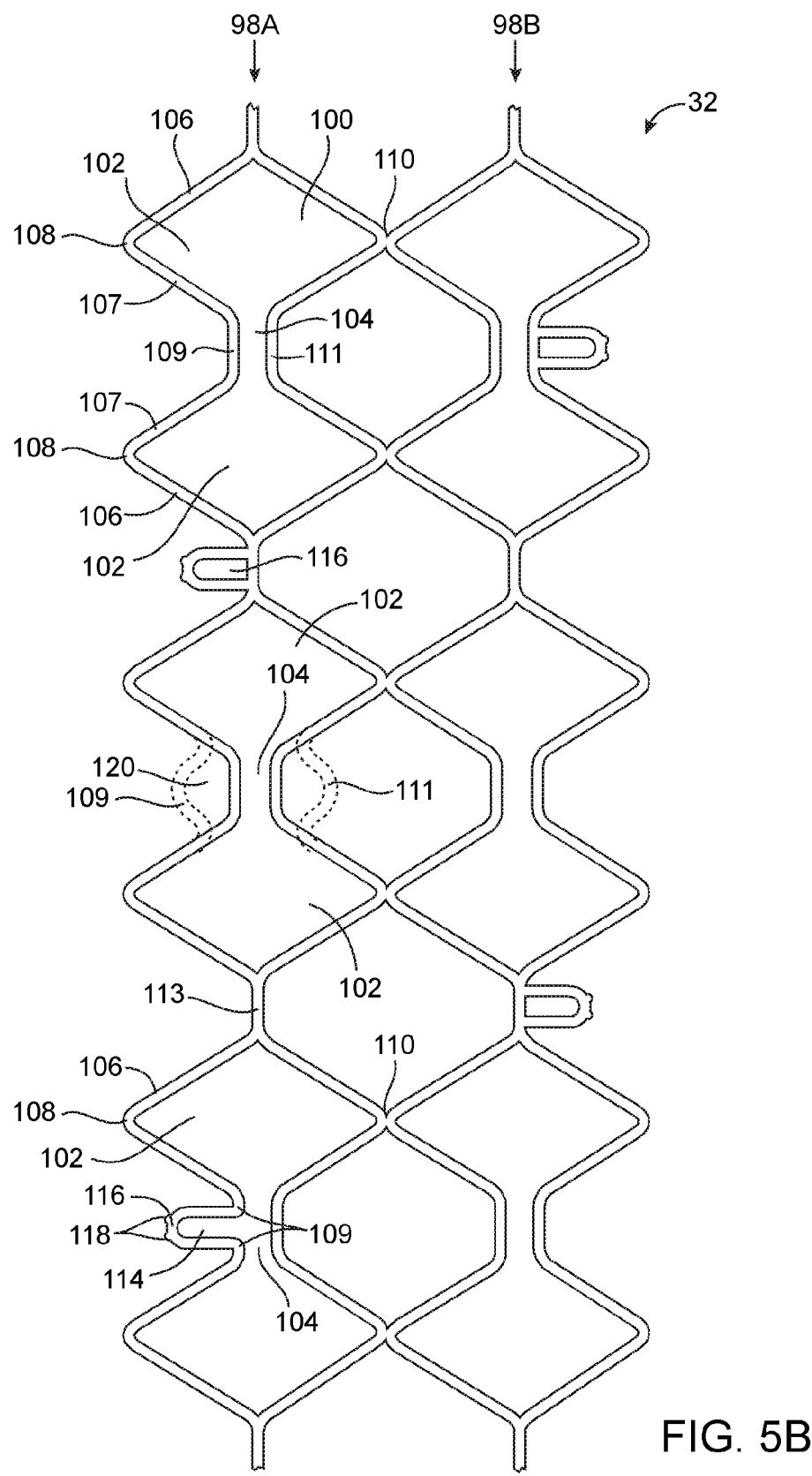
FIG. 5B is a side view of the stent segment of FIG. 5A in an expanded configuration.

In order to confirm the positioning of stent segments 32 on expandable member 24, fluoroscopy is used to visualize stent segments 32 relative to markers 82 on inner shaft 27. In addition, by fluoroscopic visualization of markers 56 on sheath 25 the user can see the extent of retraction of sheath 25 relative to expandable member 24 and view the location of the exposed stent segments 32 relative to sheath 25. Visualization of stent segments 32 is further enhanced with the use of radiopaque markers and/or materials in or on the stent segments themselves. Markers of radiopaque materials may be applied to the exterior of stent segments 32, e.g., by applying a metal such as gold, platinum, a radiopaque polymer, or other suitable coating or mark on all or a portion of the stent segments. Alternatively, stent segments 32 may include a radiopaque cladding or coating or may be composed of radiopaque materials such as L-605 cobalt chromium (ASTM F90), other suitable alloys containing radiopaque elements, or multilayered materials having radiopaque layers. In yet another alternative, stent segments 32 may have a geometry conducive to fluoroscopic visualization, such as having struts of greater thickness, sections of higher density, or overlapping struts. Some of the possible materials that may be used in stent segments 32 include (by ASTM number):

F67-00 Unalloyed Titanium
F75-01 Cobalt-28 Chromium-6 Molybdenum Alloy
F90-01 Wrought Cobalt-20 Chromium-15 Tungsten-10 Nickel Alloy
F136-02a Wrought Titanium-6 Aluminum-4 Vanadium ELI Alloy
F138-00, F139-00 Wrought 18 Chromium-14 Nickel-2.5 Molybdenum Stainless Steel Bar or Sheet
F560-98 Unalloyed Tantalum
F562-02 Wrought 35 Cobalt-35 Nickel-20 Chromium-10 Molybdenum Alloy
F563-00 Wrought Cobalt-20 Nickel-20 Chromium 3.5 Molybdenum-3.5 Tungsten-5 Iron Alloy
F688 Wrought Cobalt-35 Nickel-20 Chromium-10 Molybdenum Alloy
F745-00 18 Chromium-12.5 Nickel-2.5 Molybdenum Stainless Steel
F799-02 Cobalt-28 Chromium-6 Molybdenum Alloy
F961-96 Cobalt-35 Nickel-20 Chromium-10 Molybdenum Alloy
F1058-02 Wrought 40 Cobalt-20 Chromium-16 Iron-15 Nickel-7 Molybdenum Alloy
F1091-02 Wrought Cobalt-20 Chromium-15 Tungsten-10 Nickel Alloy
F1108 Titanium-6 Aluminum-4 Vanadium Alloy
F1295-01 Wrought Titanium-6 Aluminum-7 Niobium Alloy
F1314-01 Wrought Nitrogen-strengthened 22 Chromium-13 Nickel-5 Manganese-2.5 Molybdenum Stainless Steel Alloy
F1241-99 Unalloyed Titanium Wire
F1350-02 Wrought 18 Chromium-14 Nickel-2.5 Molybdenum Stainless Steel Wire
F1377-98a Cobalt-28 Chromium-6 Molybdenum Powder coating
F1472-02a Wrought Titanium-6 Aluminum-4 Vanadium Alloy
F1537-00 Wrought Cobalt-28 Chromium-6 Molybdenum Alloy
F1580-01 Titanium and Titanium-6 Aluminum-4 Vanadium Alloy Powder coating
F1586-02 Wrought Nitrogen Strengthened 21 Chromium-10 Nickel-3 Manganese-2.5 Molybdenum Stainless Steel Bar
F1713-96 Wrought Titanium-13 Niobium-13 Zirconium Alloy
F1813-01 Wrought Titanium-12 Molybdenum-6 Zirconium-2 Iron Alloy
F2063-00 Wrought Nickel-Titanium Shape Memory Alloys
F2066-01 Wrought Titanium-15 Molybdenum Alloy
F2146-01 Wrought Titanium-3 Aluminum-2.5 Vanadium Alloy Seamless Tubing
F2181-02a Wrought Stainless Steel Tubing A first preferred geometry of stent segments 32 is illustrated in FIGS. 5A-5B. FIG. 5A illustrates a portion of a stent segment 32 in an unexpanded configuration, shown in a planar shape for clarity. Stent segment 32 comprises two parallel rows 98A, 98B of I-shaped cells 100 formed around an axis A so that stent segment 32 has a cylindrical shape. Each cell 100 has upper and lower axial slots 102 aligned with the axial direction and a circumferential slot 104. Upper and lower slots 102 preferably have an oval, racetrack, rectangular or other oblong shape with a long dimension L generally parallel to axis A and a short dimension W perpendicular thereto. Axial slots 102 are bounded by upper axial struts 106 and lower axial struts 107, curved outer ends 108 and curved inner ends 110. Each circumferential slot 104 is bounded by an outer circumferential strut 109 and an inner circumferential strut 111. Each I-shaped cell 100 is connected to the adjacent I-shaped cell 100 in the same row 98A or 98B by a circumferential connecting strut 113. All or a portion of cells 100 in row 98A merge or join with cells 100 in row 98B at the inner ends 110, which are integrally formed with the inner ends 110 of the adjacent cells 100.

In a preferred embodiment, a spacing member 112 extends outwardly in the axial direction from a selected number of outer circumferential struts 109 and/or connecting struts 113. Spacing member 112 preferably itself forms a subcell 114 in its interior, but alternatively may be solid without any cell or opening therein. For those spacing members 112 attached to outer circumferential struts 109, subcell 114 preferably communicates with I-shaped cell 100. Spacing members 112 are configured to engage the curved outer ends 108 of an adjacent stent segment 32 so as to maintain appropriate spacing between adjacent stent segments. In one embodiment, spacing members 112 have outer ends 116 with two spaced-apart protrusions 118 that provide a cradle-like structure to index and stabilize the curved outer end 108 of the adjacent stent segment. Preferably, spacing members 112 have an axial length of at least about 10%, more preferably at least about 25%, of the long dimension L of I-shaped cells 100, so that the I-shaped cells 100 of adjacent stent segments are spaced apart at least that distance. Because spacing members 112 experience little or no axial shortening during expansion of stent segments 32, this minimum spacing between stent segments is maintained both in the unexpanded and expanded configurations.

FIG. 5B shows stent segment 32 of FIG. 5A in an expanded configuration. Cells 100 are expanded so that upper and lower slots 102 are diamond shaped with circumferential slots 104 remaining basically unchanged. This results in some axial shortening of the stent segment, thereby increasing the spacing between adjacent stent segments. The stent geometry is optimized by balancing the amount of axial shortening and associated inter-segment spacing, the desired degree of vessel wall coverage, the desired metal density, and other factors. Because the stent is comprised of multiple unconnected stent segments 32, any desired number from 2 up to 10 or more stent segments may be deployed simultaneously to treat lesions of any length. Further, because such segments are unconnected to each other, the deployed stent structure is highly flexible and capable of deployment in long lesions having curves and other complex shapes.

As an additional feature, circumferential slots 104 provide a pathway through which vessel side branches can be accessed for catheter interventions or for treatment of bifurcation lesions. Should stent segment 32 be deployed at a location in which it covers the ostium of a side branch to which access is desired, a balloon dilatation catheter may be positioned through circumferential slot 104 and expanded. This deforms circumferential struts 109, 111 axially outward, thereby expanding circumferential slot 104 and further expanding upper and lower slots 102, as shown in phantom in FIG. 3B. This provides a relatively large opening 120 through which a catheter may be inserted through stent segment 32 and into the side branch for placing stents, performing angioplasty, or carrying out other interventions.

Figure 6A:
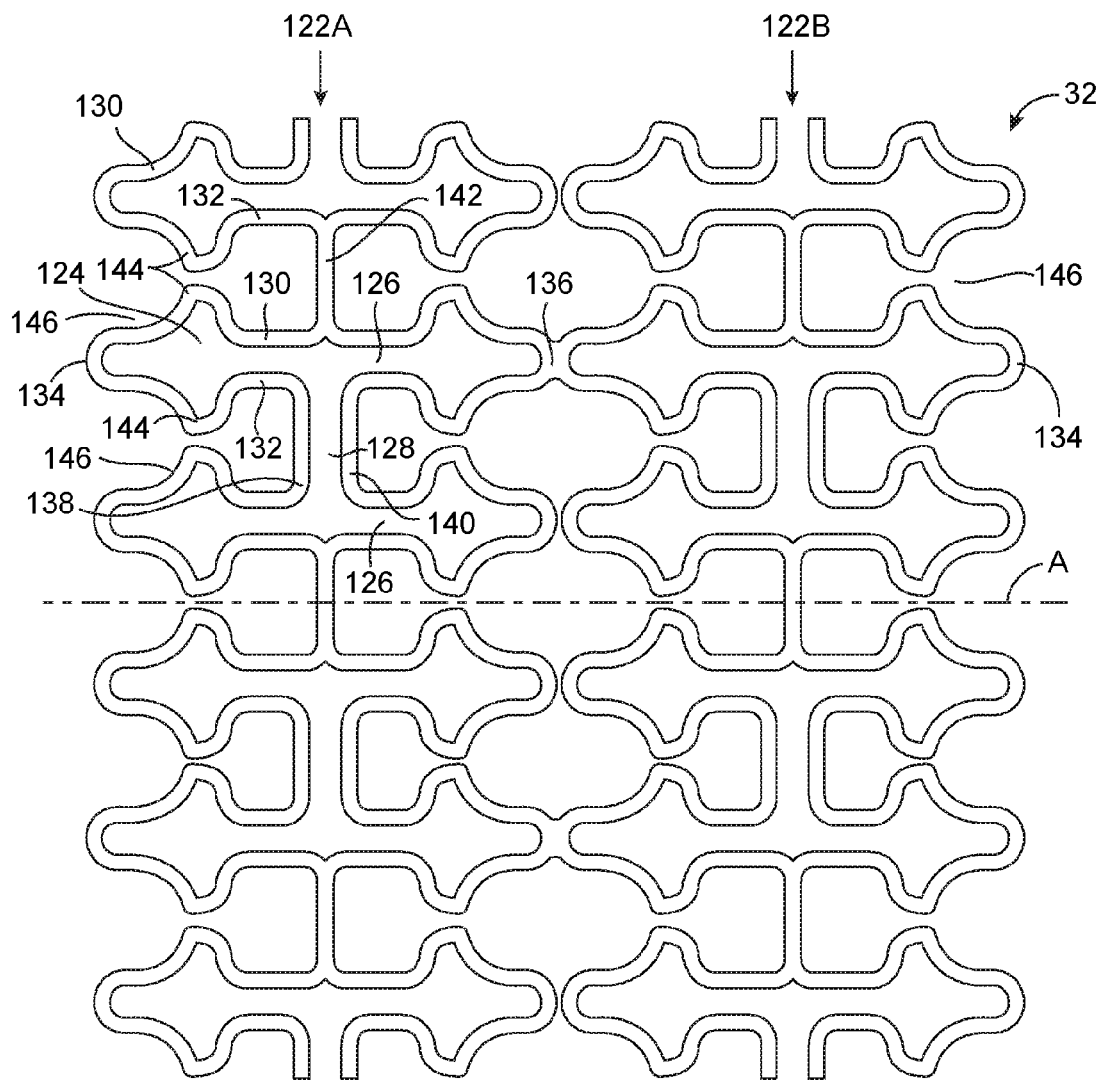
FIG. 6A is a side view of a second embodiment of a stent segment according to the invention in an unexpanded configuration.
Figure 6B:
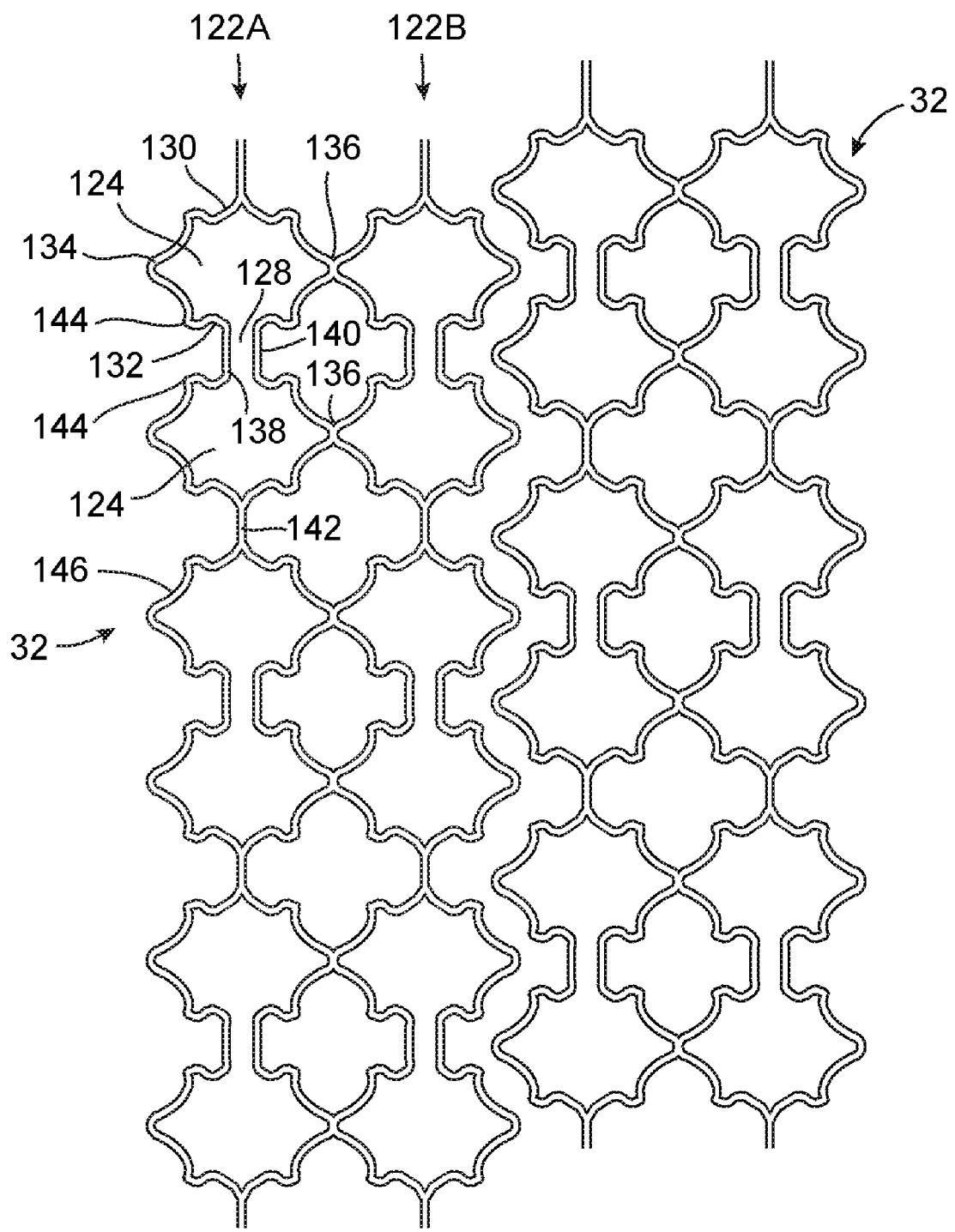
FIG. 6B is a side view of two of the stent segments of FIG. 6A in an expanded configuration.

FIGS. 6A-6B illustrate a second embodiment of a stent segment 32 according to the invention. In FIG. 6A, a portion of stent segment 32 is shown in a planar shape for clarity. Similar to the embodiment of FIG. 5A, stent segment 32 comprises two parallel rows 122A, 122B of I-shaped cells 124 formed into a cylindrical shape around axial axis A. Cells 124 have upper and lower axial slots 126 and a connecting circumferential slot 128. Upper and lower slots 126 are bounded by upper axial struts 130, lower axial struts 132, curved outer ends 134, and curved inner ends 136. Circumferential slots 128 are bounded by outer circumferential strut 138 and inner circumferential strut 140. Each I-shaped cell 124 is connected to the adjacent I-shaped cell 124 in the same row 122 by a circumferential connecting strut 142. Row 122A is connected to row 122B by the merger or joining of curved inner ends 136 of at least one of upper and lower slots 126 in each cell 124.

One of the differences between the embodiment of FIGS. 6A-6B and that of FIGS. 5A-5B is the way in which spacing is maintained between adjacent stent segments. In place of the spacing members 112 of the earlier embodiment, the embodiment of FIG. 6A includes a bulge 144 in upper and lower axial struts 130, 132 extending circumferentially outwardly from axial slots 126. These give axial slots 126 an arrowhead or cross shape at their inner and outer ends. The bulge 144 in each upper axial strut 130 extends toward the bulge 144 in a lower axial strut 132 in the same cell 100 or in an adjacent cell 100, thus creating a concave abutment 146 in the space between each axial slot 126. Concave abutments 146 are configured to receive and engage curved outer ends 134 of cells 124 in the adjacent stent segment, thereby maintaining spacing between the stent segments. The axial location of bulges 144 along upper and lower axial struts 130, 132 may be selected to provide the desired degree of inter-segment spacing.

FIG. 6B shows two stent segments 32 of FIG. 6A in an expanded condition. Axial slots 124 are deformed into a circumferentially widened modified diamond shape with bulges 144 on the now diagonal upper and lower axial struts 130, 132. Circumferential slots 128 are generally the same size and shape as in the unexpanded configuration. Bulges 144 have been pulled away from each other to some extent, but still provide a concave abutment 146 to maintain a minimum degree of spacing between adjacent stent segments. As in the earlier embodiment, some axial shortening of each segment occurs upon expansion and stent geometry can be optimized to provide the ideal intersegment spacing.

The embodiment of FIGS. 6A-6B retains the feature described above with respect to FIGS. 5A-5B to enable access to vessel side branches blocked by stent segment 32. Should such side branch access be desired, a dilatation catheter may be inserted into circumferential slot 128 and expanded to provide an enlarged opening through which a side branch may be entered.

Referring now to FIGS. 7A-7E, the use of the stent delivery catheter of the invention will be described. While the invention will be described in the context of coronary artery treatment, the invention is useful in any of a variety of blood vessels and other body lumens in which stents are deployed, including the carotid, renal, femoral, iliac and other arteries, as well as veins, grafts, biliary ducts and other fluid-carrying vessels. A guiding catheter (not shown) is first inserted into a peripheral artery such as the femoral and advanced to the ostium of the target coronary artery. A guidewire GW is then inserted through the guiding catheter into the coronary artery A where lesion L is to be treated. The proximal end of guidewire GW is then inserted through nosecone 28 and guidewire tube 34 outside the patient's body and stent delivery catheter 20 is slidably advanced over guidewire GW and through the guiding catheter into the coronary artery A. Stent delivery catheter 20 is positioned through a lesion L to be treated such that nosecone 28 is distal to lesion L. During this positioning, sheath 25 is positioned distally up to nosecone 28 so as to surround expandable member 24 and all of the stent segments 32 thereon.

Optionally, lesion L may be predilated prior to stent deployment. Predilatation may be performed prior to introduction of stent delivery catheter 20 by inserting an angioplasty catheter over guidewire GW and dilating lesion L. Alternatively, stent delivery catheter 20 may be used for predilitation by retracting sheath 25 along with stent segments 32 to expose an extremity of expandable member 24 long enough to extend through the entire lesion. This may be done while delivery catheter 20 is positioned proximally of lesion L or with expandable member 24 extending through lesion L. Fluoroscopy enables the user to visualize the extent of sheath retraction relative to lesion L by observing the position of marker 56 on sheath 25 relative to marker 82 at the distal end of expandable member 24. To allow stent segments 32 to move proximally relative to expandable member 24, force is released from pusher tube 86 and valve member 58 engages and draws the stent segments proximally with sheath 25. With the appropriate length of expandable member 24 exposed, expandable member 24 is positioned within lesion L and inflation fluid is introduced through inflation lumen 66 to inflate expandable member 24 distally of sheath 25 and thereby dilate lesion L. Expandable member 24 is then deflated and retracted within sheath 25 while maintaining force on pusher tube 86 so that stent segments 32 are positioned up to the distal end of expandable member 24, surrounded by sheath 25.

Following any predilatation, stent delivery catheter 20 is repositioned in artery A so that nosecone 28 is distal to lesion L as shown in FIG. 7A. Sheath 25 is then retracted as in FIG. 7B to expose the appropriate number of stent segments 32 to cover lesion L. Again, fluoroscopy can be used to visualize the position of sheath 25 by observing marker 56 thereon relative to marker 82 within expandable member 24. As sheath 25 is drawn proximally, force is maintained against pusher tube 86 so that stent segments 32 remain positioned up to the distal end of expandable member 24. It should also be noted that sheath 25 moves proximally relative to guidewire tube 34, which slides through guidewire tube exit port 35. Advantageously, regardless of the position of sheath 25, guidewire tube 34 provides a smooth and continuous passage for guidewire GW so that stent delivery catheter slides easily over guidewire GW.

With the desired number of stent segments 32 exposed distally of sheath 25, it is frequently desirable to create some spacing between the stent segments to be deployed and those remaining enclosed within sheath 25. This reduces the risk of dislodging or partially expanding the distal-most stent segment 32 within sheath 25 when expandable member 24 is inflated. Such spacing is created, as shown in FIG. 7C, by releasing force against pusher tube 86 and retracting sheath 25 further proximally a short distance. The engagement of valve member 58 with stent segments 32 moves those stent segments 32 within sheath 25 away from those stent segments 32 distal to sheath 25. The length of this spacing is preferably equal to the length of about ½-1 stent segment.

Expandable member 24 is then inflated by delivering inflation fluid through inflation lumen 66, as shown in FIG. 7D. The exposed distal portion of expandable member 24 expands so as to expand stent segments 32 thereon into engagement with lesion L. If predilatation was not performed, lesion L may be dilated during the deployment of stent segments 32 by appropriate expansion of expandable member 24. Sheath 25 constrains the expansion of the proximal portion of expandable member 24 and those stent segments 32 within sheath 25.

Figure 8:
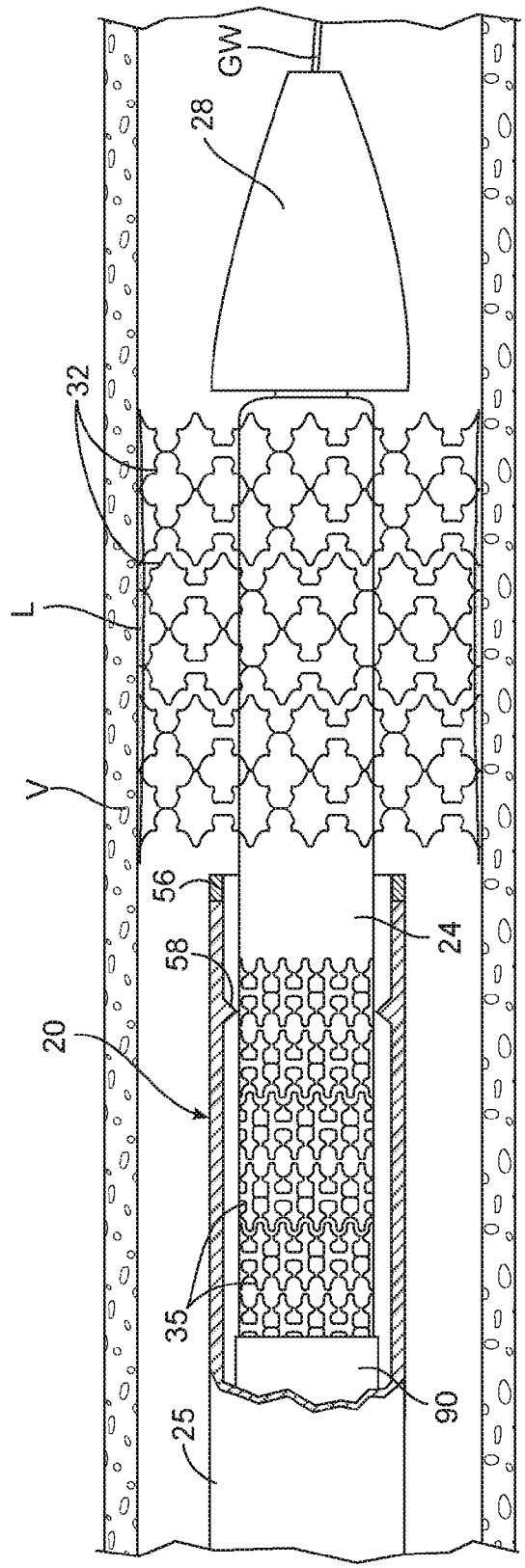
FIG. 8 is a side cut-away view of the stent delivery catheter of the invention positioned in a vessel with the stent segments of FIGS. 6A-6B in a deployed configuration.

Expandable member 24 is then deflated, leaving stent segments 32 in a plastically-deformed, expanded configuration within lesion L, as shown in FIG. 7E. The alternative embodiment of stent segment 32 illustrated in FIGS. 6A-6B is shown in a similarly expanded condition in FIG. 8. With stent segments 32 deployed, expandable member 24 may be retracted within sheath 25, again maintaining force against pusher tube 86 to position stent segments 32 at the distal end of expandable member 24. Expandable member 24 is moved proximally relative to stent segments 32 until the distal-most stent segment engages stop 78 (FIGS. 2A-2B), thereby placing stent segments 32 in position for deployment. Stent delivery catheter 20 is then ready to be repositioned at a different lesion in the same or different artery, and additional stent segments may be deployed. During such repositioning, guidewire tube 34 facilitates smooth tracking over guidewire GW. Advantageously, multiple lesions of various lengths may be treated in this way without removing stent delivery catheter 20 from the patient's body. Should there be a need to exchange stent delivery catheter 20 with other catheters to be introduced over guidewire GW, guidewire tube 34 facilitates quick and easy exchanges.

When the movement of the pusher tube, sheath, or stent segments is described in relation to other components of the delivery catheter of the invention, such movement is relative and will encompass moving the sheath, pusher tube, or stent segments while keeping the other component(s) stationary, keeping the sheath, pusher tube or stent segments stationary while moving the other component(s), or moving multiple components simultaneously relative to each other.

As described above in reference to FIGS. 2A and 2B, some embodiments of a catheter device include a stent stop 78 for stopping advancement of stents over an expandable member 24, thus helping position the stents in a desired location over the expandable member 24 for deployment. As shown in FIGS. 9-19, and as described immediately below, various embodiments of catheter devices may include stent stops having any of a variety of configurations, sizes, materials and/or the like. In FIGS. 9-19, the labeling numbers of the distal end of the catheter device are the same as those used in FIGS. 2A and 2B, except with relation to the various stent stops or unless otherwise described.

Figure 9:
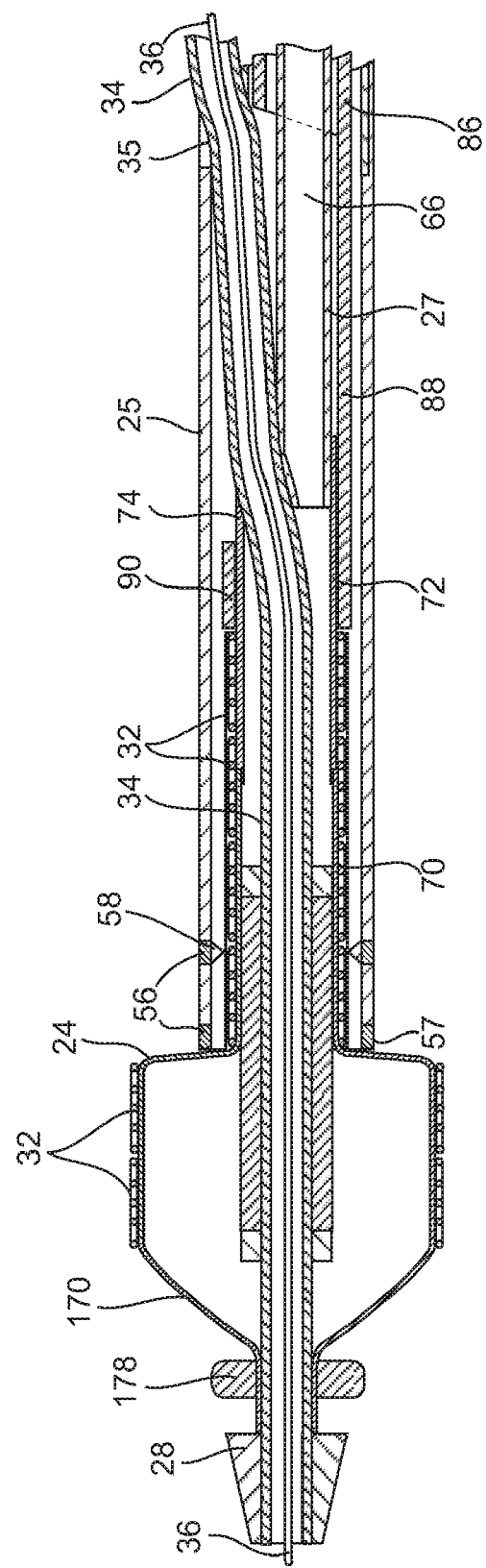
FIG. 9 is a side cross-section of a distal portion of a stent delivery catheter having a stent stop, with expandable member inflated and sheath retracted according to one embodiment of the present invention.

Referring now to FIG. 9, one embodiment of a delivery catheter includes a stent stop 178 that resides outside the expandable member 24. Such a stent stop 178 may have the shape of a cylinder, ring, disk, sleeve, cone or the like. The stop 178 may be positioned distally of the a distal taper 170 in the expandable member or may be mounted so as to be positioned just at the distal end of the cylindrically shaped deployment portion 179 of expandable member 24.

Figure 10:
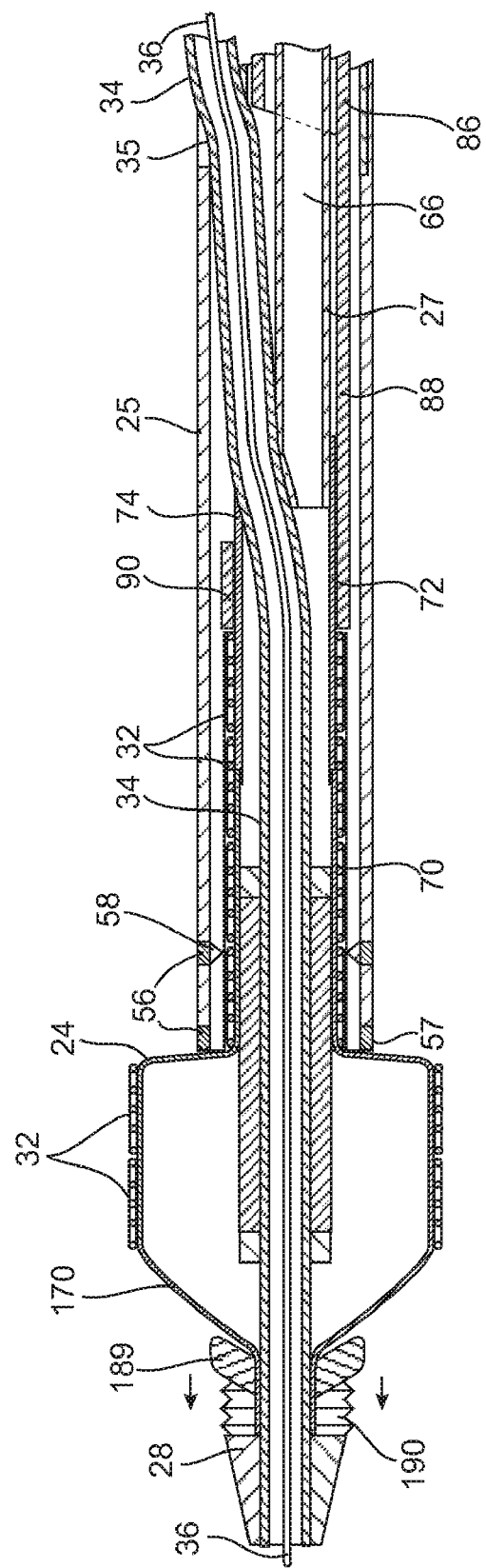
FIG. 10 is a side cross-section of a distal portion of a stent delivery catheter having a stent stop, with expandable member inflated and sheath retracted according to another embodiment of the present invention.

An alternative embodiment, pictured in FIG. 10, includes a stent stop comprising a cone 189 (or ring, sleeve, cylinder or the like) and a spring-loaded sleeve 190 disposed between the ring 189 and the sleeve 190. When the expandable member 24 is expanded, it pushes the cone 189 forward (distally), off of the distal taper 170 (solid tipped arrows). When the expandable member 24 is deflated, the spring loaded sleeve 190 pushes the cone 189 back (proximally) such that it will be positioned to stop advancement of the stent segments 32. Thus, the stent stop operates to stop the stent segments 32 on a portion of the expandable member 24 just proximal the distal taper 170 and then is advanced off of the distal taper with inflation/expansion of the expandable member 24. When the expandable member 24 is then deflated, the spring loaded member 190 pushes the cone 189 proximally again, to its position for stopping stent segments 32.

Figure 11:
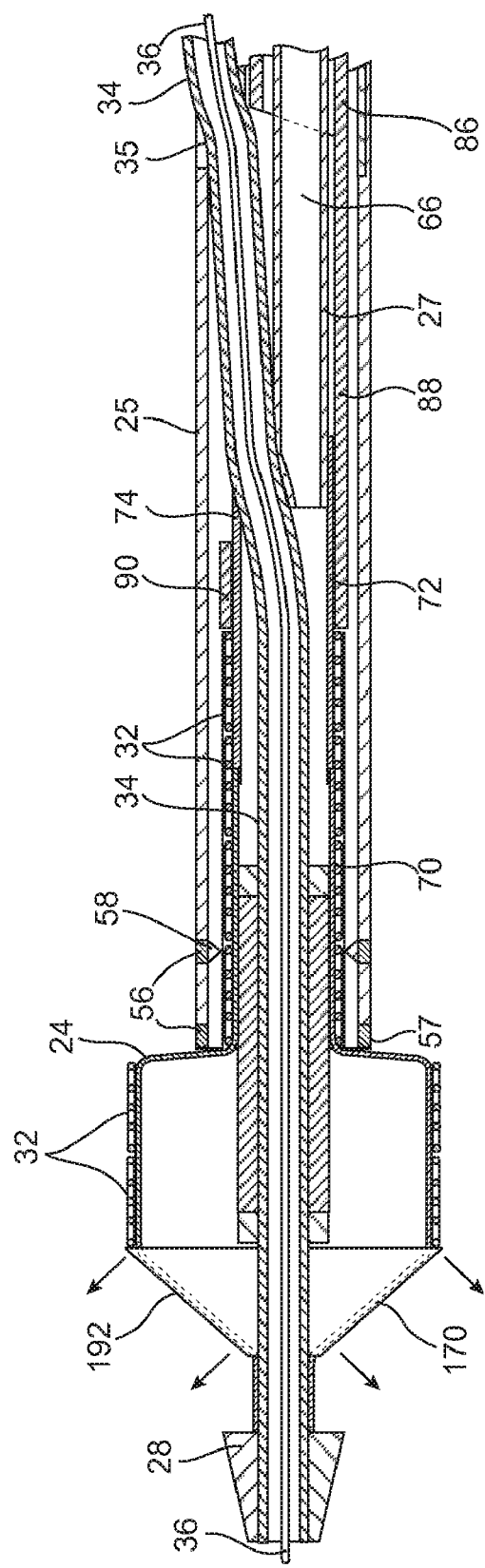
FIG. 11 is a side cross-section of a distal portion of a stent delivery catheter having a stent stop, with expandable member inflated and sheath retracted according to another embodiment of the present invention.

Referring now to FIG. 11, in another embodiment a stent stop 192 may be radially expandable, such as a radially expandable cone that fits over the distal taper 170 of the expandable member 24. Such a stent stop 192 may be constructed of any suitable elastic or resilient material or combination of materials, such as an elastomer or a woven or elastically deformable metal such as Nitinol or any other shape-memory or super-elastic material. As the expandable member 24 expands, the stent stop 192 expands as well (solid tipped arrows). When the expandable member 24 deflates, the stent stop 192 elastically returns to its unexpanded state. The stent stop 192 may have a cone shape as shown, or may be a ring, cylinder or have any other suitable shape, size or configuration.

Figure 11A:
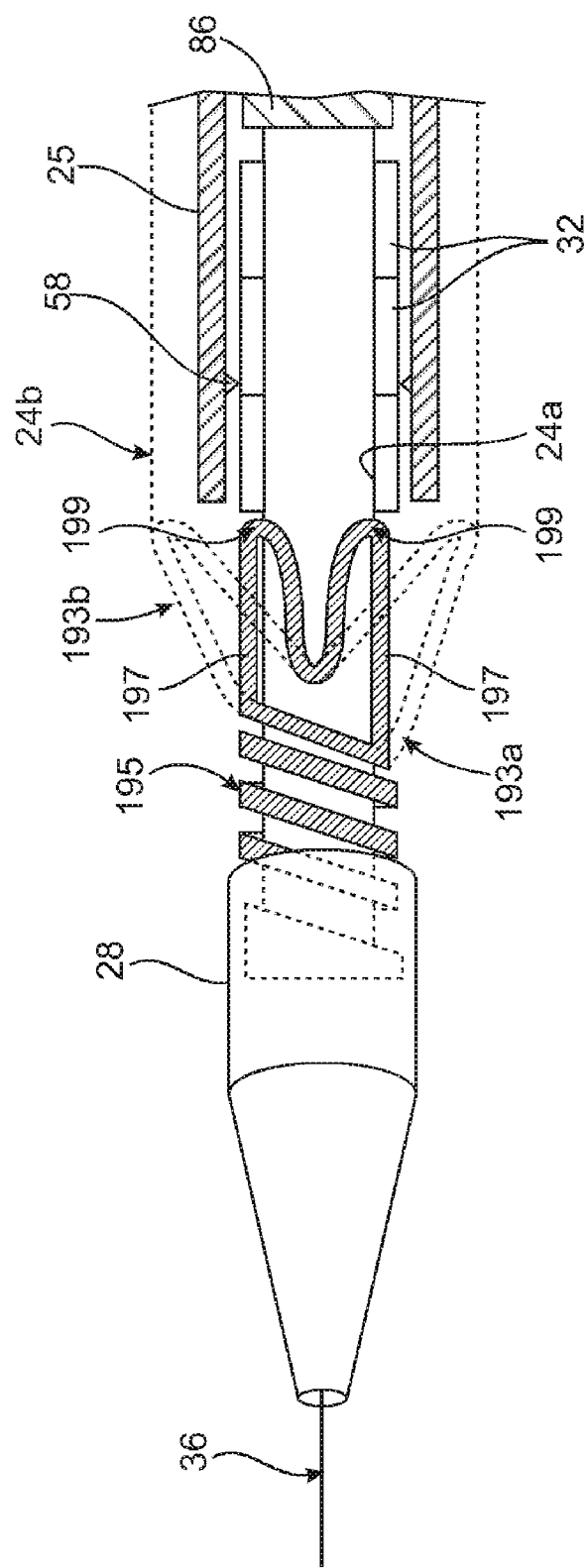
FIG. 11A is a side partial-cross-section of a distal portion of a stent delivery catheter having a stent stop, with expandable member shown in inflated and deflated configurations according to another embodiment of the present invention.

In another embodiment, shown in FIG. 11A, an expandable stent stop 193 comprises a wire or ribbon of resilient or shape memory material formed into a plurality (e.g., 2, 4, 6 or more) projections 197 that normally reside parallel to the axial direction and have tips 199 projecting proximally so as to engage stent segments 32 when expandable member 24a is unexpanded. Projections 197 have a length selected so as to cover the distal taper of expandable member 24a. Stent stop 193 expands and collapses along with expandable member 24. When expandable member 24a is unexpanded, stent stop 193a is in its collapsed state and fits within sheath 25. When expandable member 24b is expanded (dotted lines), projections 197 are deflected outwardly along with it. Optionally, stent stop 193 may be coupled to or formed integrally with a compression spring 195, which provides some amount of cushion when stent segments 32 contact the stent stop 193. Spring 195 allows stent segments 32 to be pushed distally against stent stop 193a, thus compressing spring 195. Spring 195 then recoils to position the stent segments 32 in a proper location, just proximal to the distal tapered portion of expandable member 24.

Figure 11B:
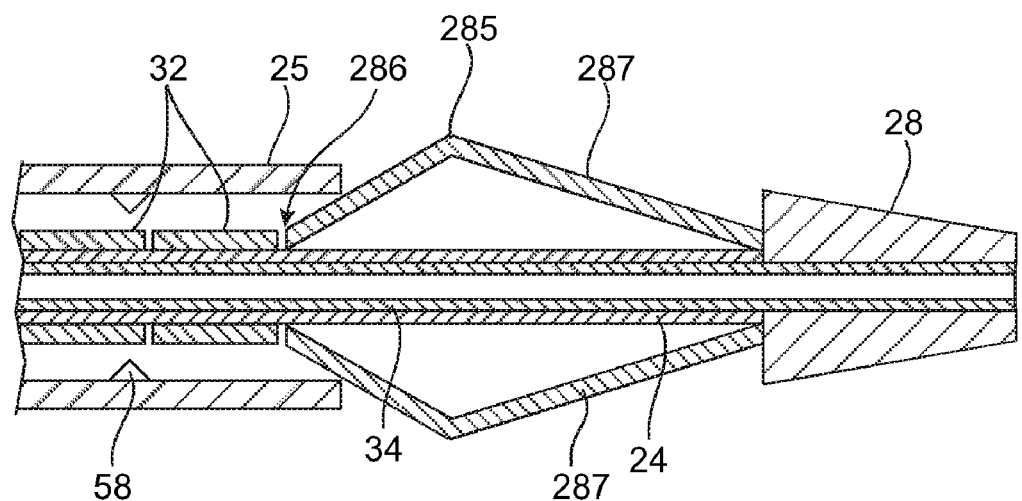
FIGS. 11B and 11C are partial-cross-sections of a distal portion of a stent delivery catheter having a resilient, collapsible stent stop according to another embodiment of the present invention.
Figure 11C:
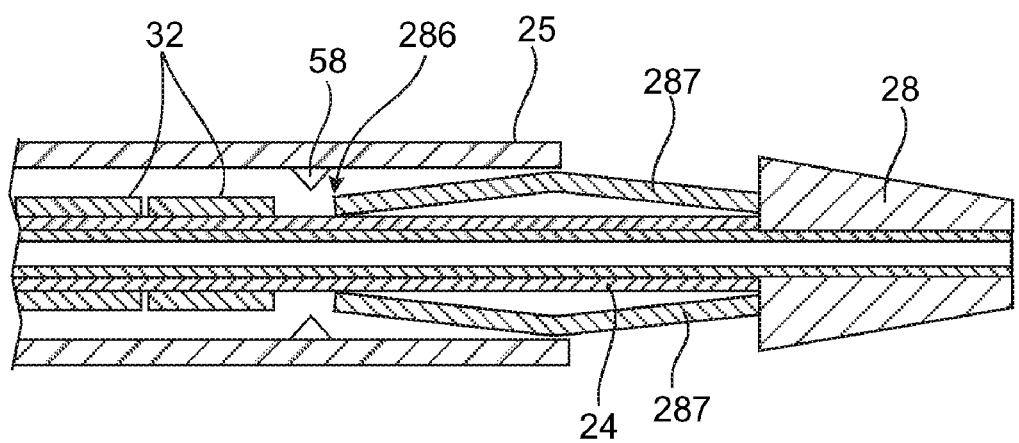

Referring now to FIG. 11B, another embodiment of a stent delivery device includes a stent stop 287 having a flexible bias or bend formed by at least one flex point 285. When sheath 25 is retracted proximally, as in FIG. 11B, flex point 285 creates a bias in stent stop 287 to help assure that a proximal end 286 of stent stop 287 is disposed within sheath 25 and does not get caught on the distal end of sheath 25. Thus, when sheath 25 is advanced and/or stent stop 287 is retracted into sheath 25, as in FIG. 11C, stent stop proximal end 286 slides within sheath 25 without catching on or abutting the distal end of sheath 25. When expandable member 24 is expanded (not shown), stent stop 287 expands along with it and is sufficiently resilient to resume its unexpanded, biased shape when the expandable member 24 is deflated. Stent stop 287 may be manufactured from any suitable resilient material or combination of materials, such as but not limited to shape memory or super-elastic materials, elastomers, polymers, or the like. In some embodiments, for example, C-flex polymer or Nitinol may be used. In one embodiment, as shown, stent stop 287 comprises a one-piece member. In other embodiments, however, stent stop 287 may comprise a plurality of arms or projections, similar to those described with reference to FIG. 11A.

Figure 11D:
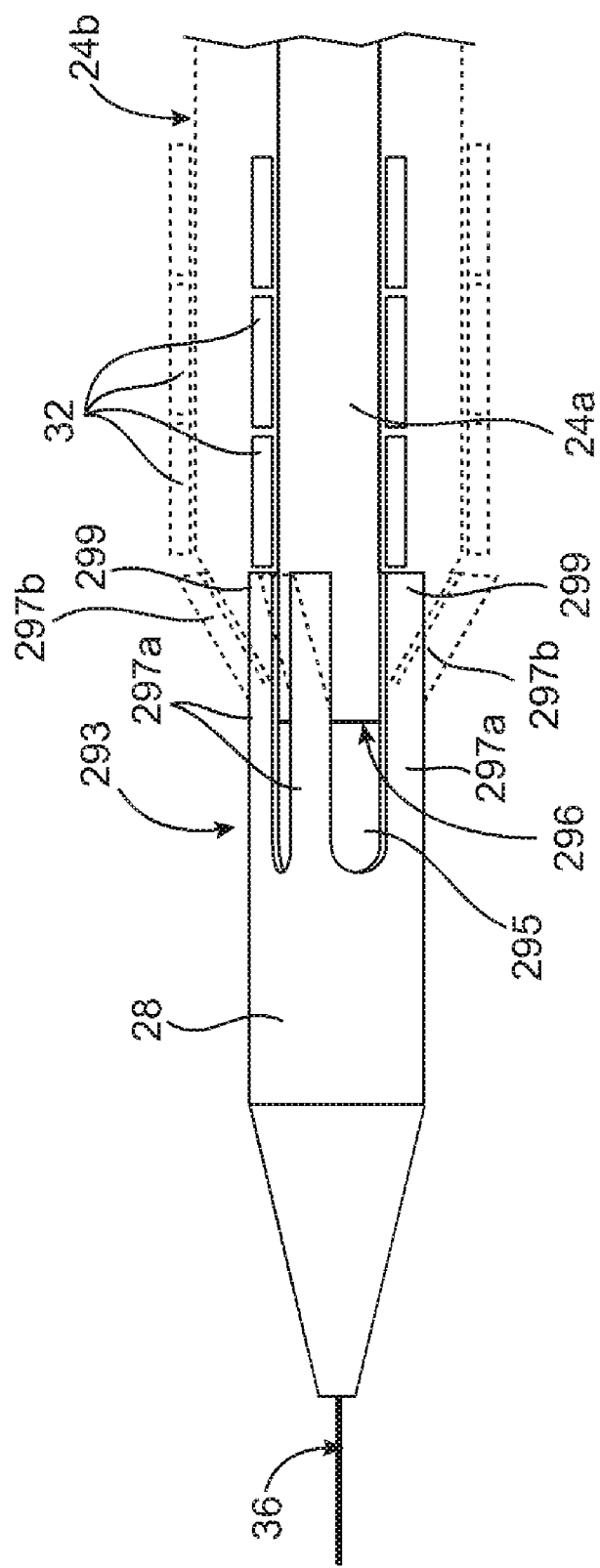
FIG. 11D is a side view of a distal portion of a stent delivery catheter having a stent stop, with expandable member shown in inflated and deflated configurations according to another embodiment of the present invention.

Referring now to FIG. 11D, an embodiment of a stent delivery device similar to that described in reference to FIG. 11A includes a stent stop 293 having a sleeve 295 disposed over the distal taper of the expandable member, to prevent the distal taper portion from expanding. Stent stop 293 further includes a plurality of projections 297 around the periphery of sleeve 295, which normally reside parallel to the axial direction and have tips 299 projecting proximally to engage stent segments 32 when expandable member 24a is unexpanded. Projections 297 have a length selected to cover the distal taper of expandable member 24a and to extend proximally beyond a proximal end 296 of the distal taper. As shown by the dotted lines in FIG. 11D, while sleeve 295 is resistant to expansion, projections 297b are sufficiently resilient to expand with expandable member 24b. Thus, sleeve 295 constrains the distal taper from expanding, expandable member 24b expands just proximal to the distal taper, and a portion of projections 297b expand with expandable member 24b. It can be seen that projections 297b create a gentle taper in expandable member 24b proximal to sleeve 295 but position stent segments 32 proximal to this tapered region so they may be fully expanded by expandable member 24. Sleeve 295 and projections 297 may be separate structures or integrally interconnected and may be made of any suitable material, such as Nitinol, stainless steel, other metals, polymers or the like.

Figure 11E:
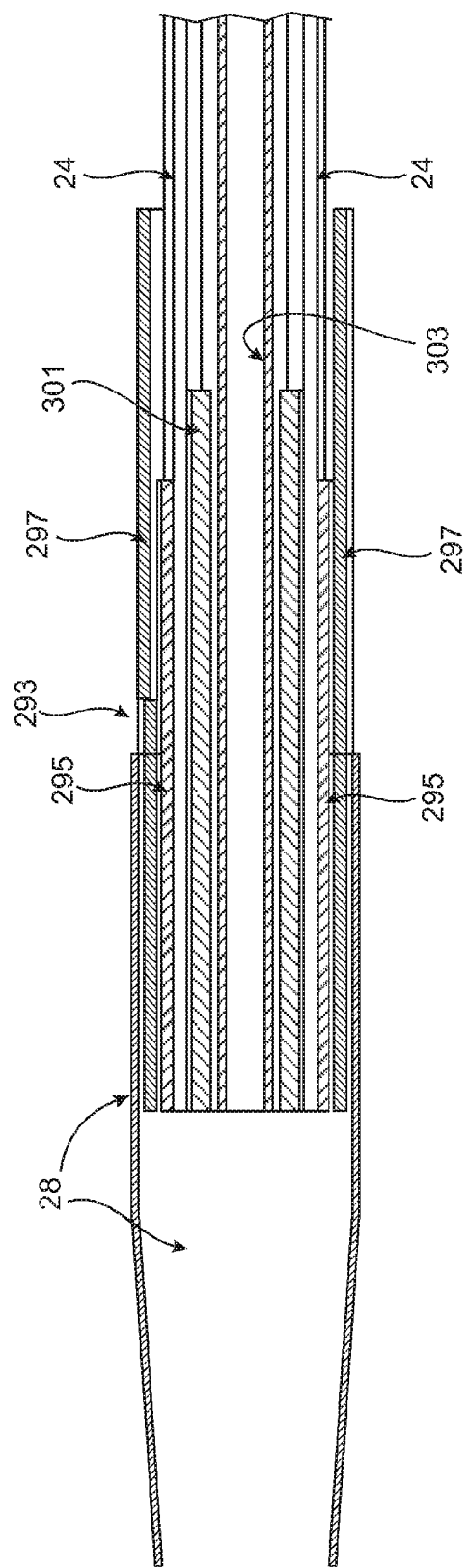
FIG. 11E is a side cross-section of the distal portion shown in FIG. 11D.

FIG. 11E shows a distal portion of the stent delivery device of FIG. 11D in cross section, with the sheath removed for clarity. As shown, in one embodiment sleeve 295 and projections 297 may extend distally under nosecone 28 and may be secured thereto by bonding or other suitable means. Alternatively, sleeve 295 and/or projections 297 may be integrally formed with nosecone 28 as a single molded or machined part. The device also includes a cylindrical mounting member 301 to which expandable member 24 is attached, via bonding with adhesive or the like. A guidewire tube 303 extends through the device to provide for passage of a guidewire.

Figure 12:
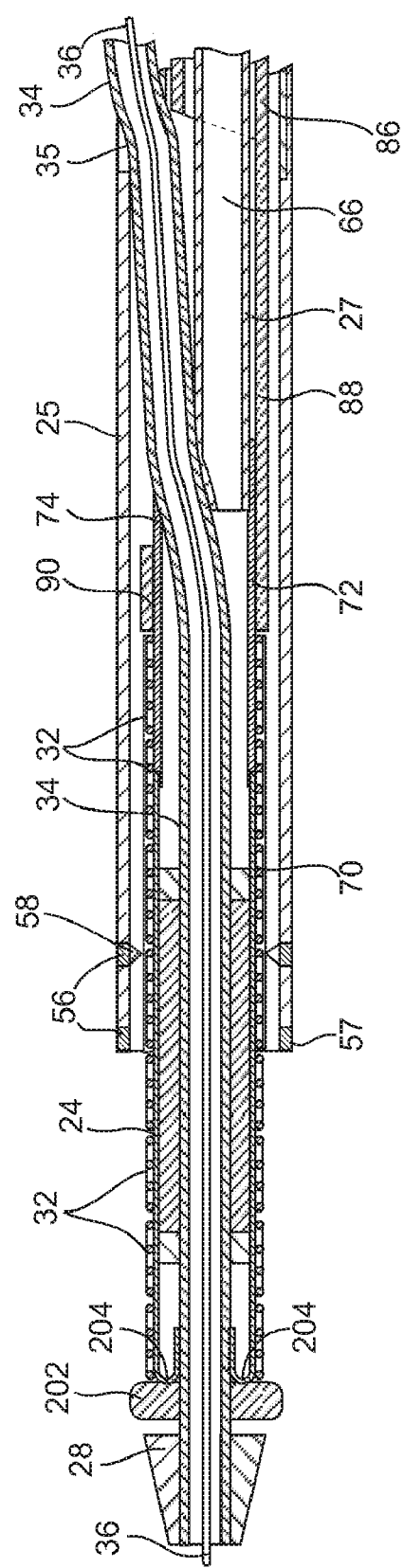
FIG. 12 is a side cross-section of a distal portion of a stent delivery catheter having a stent stop, with expandable member inflated and sheath retracted according to another embodiment of the present invention.
Figure 13:
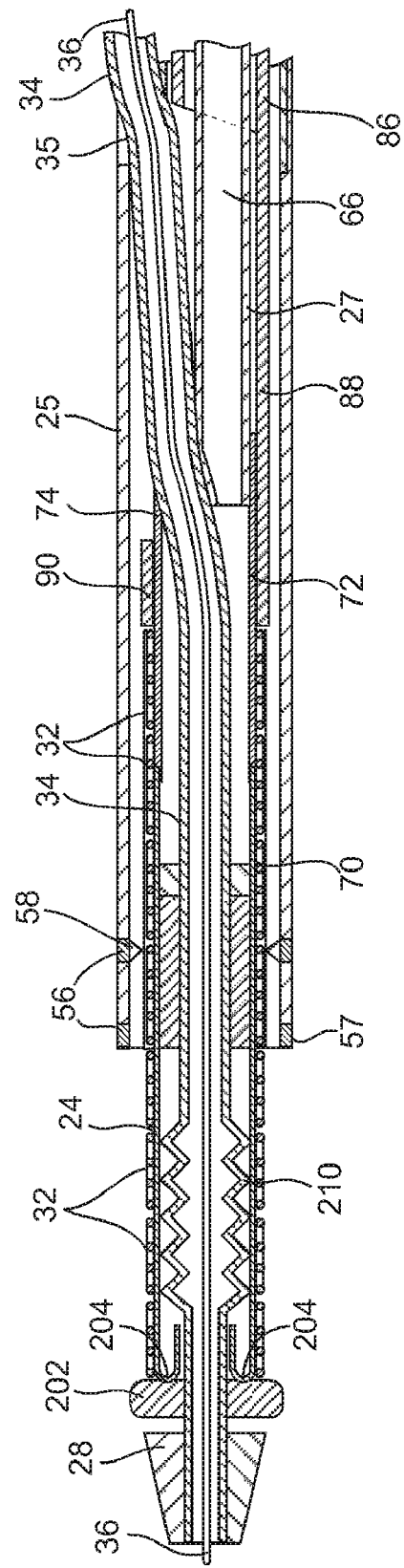
FIG. 13 is a side cross-section of a distal portion of a stent delivery catheter having a stent stop, with expandable member inflated and sheath retracted according to another embodiment of the present invention.

Another alternative embodiment is shown in FIG. 12, with the expandable member 24 in its unexpanded state. This embodiment includes a stent stop 202 and an expandable member 24 having an everted portion 204 toward its distal end, the distal end of the everted portion being attached to the guidewire tube 34. In the unexpanded state, the stent segments 32 are advanced until the distal most stent abuts the stent stop 202. Upon inflation of the expandable member 24, the everted portion 204 becomes the tapered portion 170, shown in FIG. 9. Advantageously, stent segments 32 remain positioned on the cylindrically shaped deployment portion 205 of expandable member 24, just proximal to distal taper 204. In a similar embodiment, pictured in FIG. 13, the expandable member 24 has a distal everted portion 204 adjacent the stent stop 202, and the guidewire tube 34 includes a spring section 210. The spring section 210 is compressed when the expandable member 24 is deflated and extends when the expandable member 24 is inflated. This spring action allows the distal end of the expandable member 24 to move distally as the expandable member 24 expands, thus keeping the stent segments 32 in a constant position relative to the catheter body.

Figure 14:
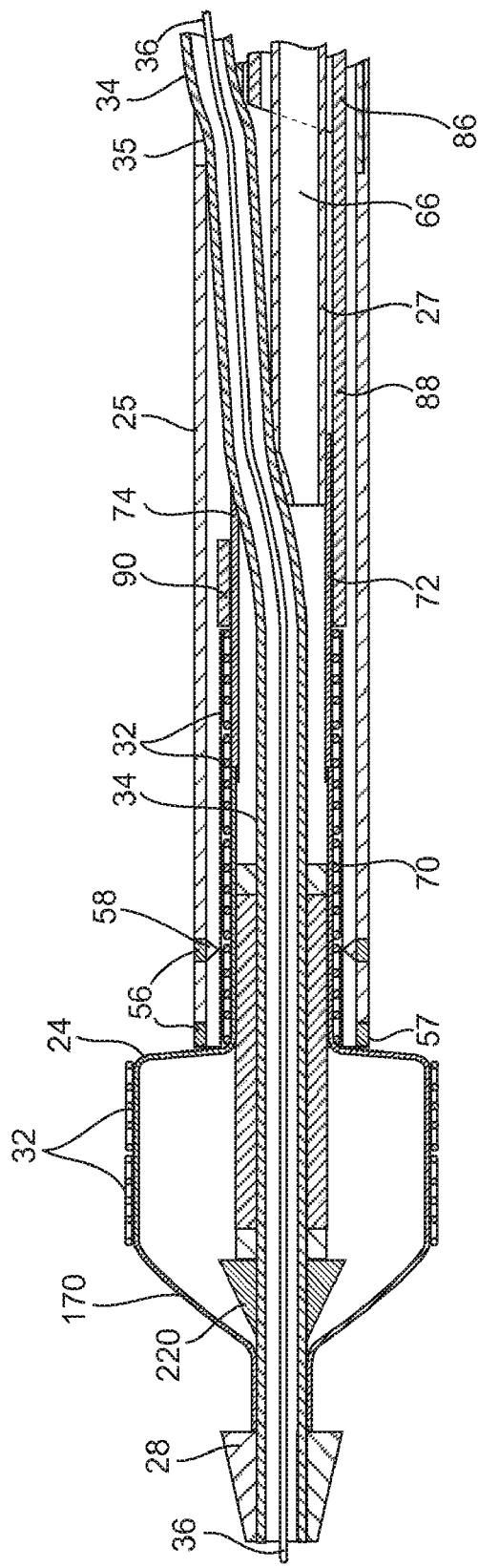
FIG. 14 is a side cross-section of a distal portion of a stent delivery catheter having a stent stop, with expandable member inflated and sheath retracted according to another embodiment of the present invention.
Figure 15:
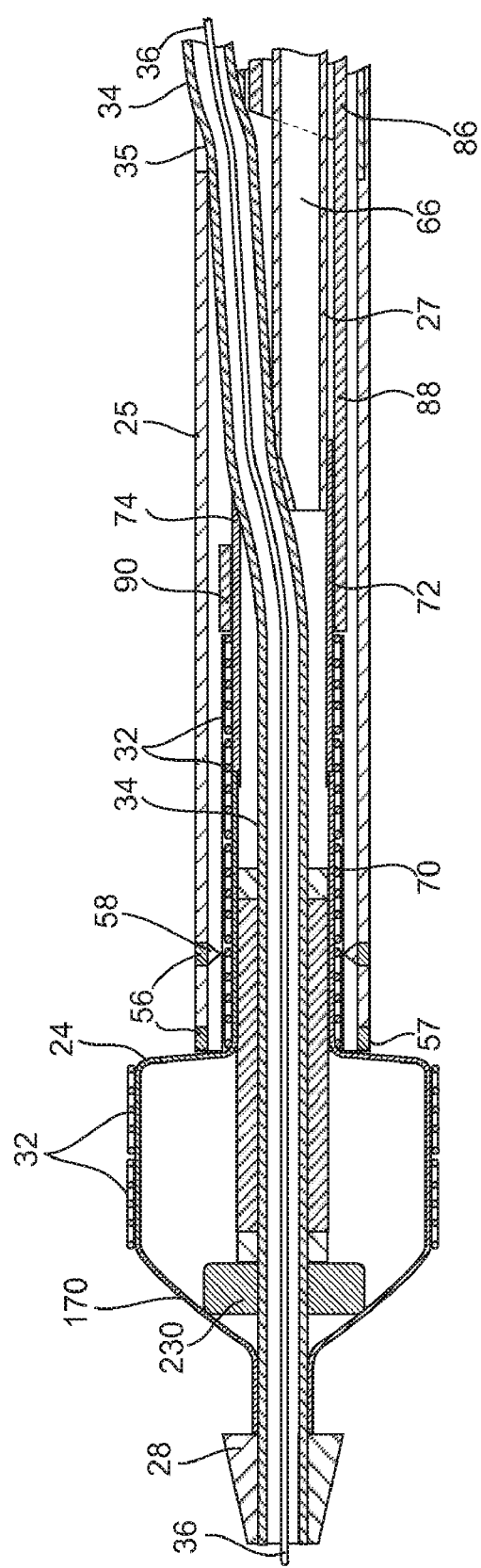
FIG. 15 is a side cross-section of a distal portion of a stent delivery catheter having a stent stop, with expandable member inflated and sheath retracted according to another embodiment of the present invention.

Referring to FIG. 14, in another embodiment of a delivery catheter a conical stent stop 220 may be disposed within the expandable member 24. Stent stop 220 may have a conical shape, as shown, or another suitable shape such as cylindrical or a reverse cone that tapers proximally. Stent stop 220 is configured to allow stent segments 32 to slide over it and stop due to frictional engagement. The stent stop 220 in this embodiment is attached to the guidewire tube 34 by any suitable means. In an alternative embodiment, shown in FIG. 15, another configuration of a cylindrical stent stop 230 disposed within the expandable member 24 is sized larger than stent segments 32, engaging the distal end of stent segments 32. Stent stop 230 may also engage the distal end of the sheath 25 when it is advanced over expandable member 24.

Figure 16:
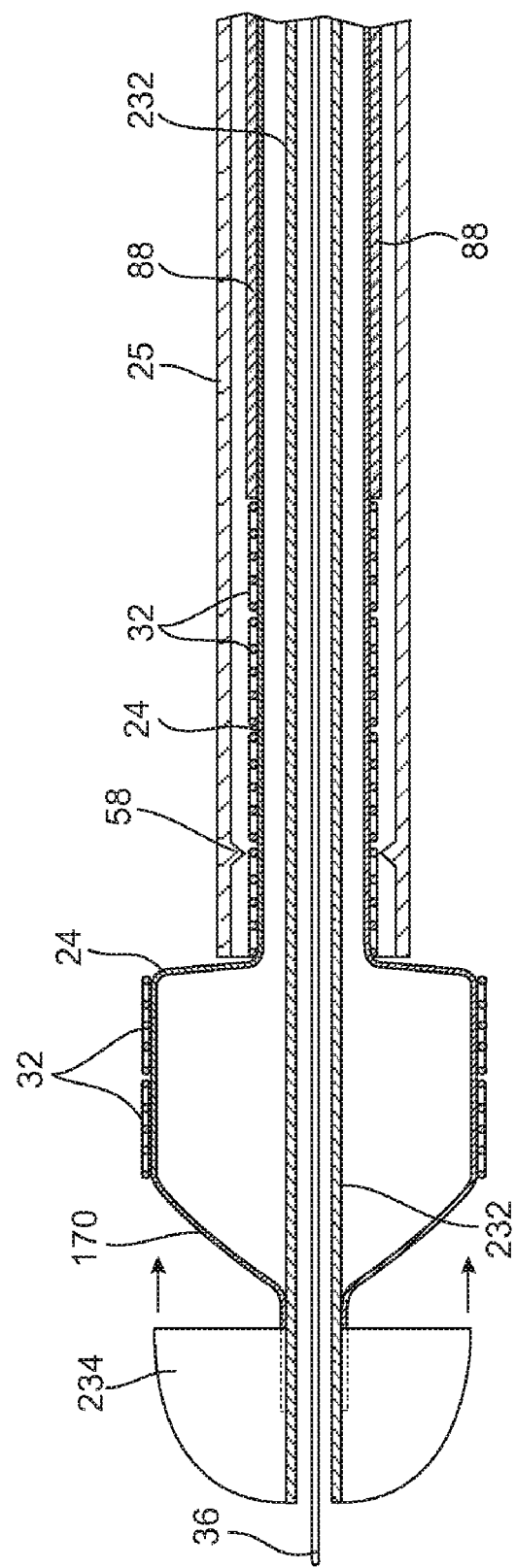
FIG. 16 is a side cross-section of a distal portion of a stent delivery catheter having a stent stop, with expandable member inflated and sheath retracted according to another embodiment of the present invention.

With reference now to FIG. 16, in another embodiment a delivery catheter includes a stent stop 234 attached to an axially movable inner catheter shaft 232, which may also serve as a guidewire tube. The stent stop 234 is shaped as a capsule with an open proximal end that can be positioned around the distal portion of the expandable member 24 in its unexpanded state. In this position, the stent stop 234 is used to stop and thus position the stent segments 32 proximal to distal taper 170. The stent stop 234 can then be moved distally off the end of the expandable member 24 by sliding the inner shaft 232 distally relative to the rest of the delivery catheter, thus allowing the distal taper 170 of the expandable member 24 to expand. In some embodiments, the stent stop 234 may also be used to constrain a distal portion of the expandable member from expanding.

Figure 17:
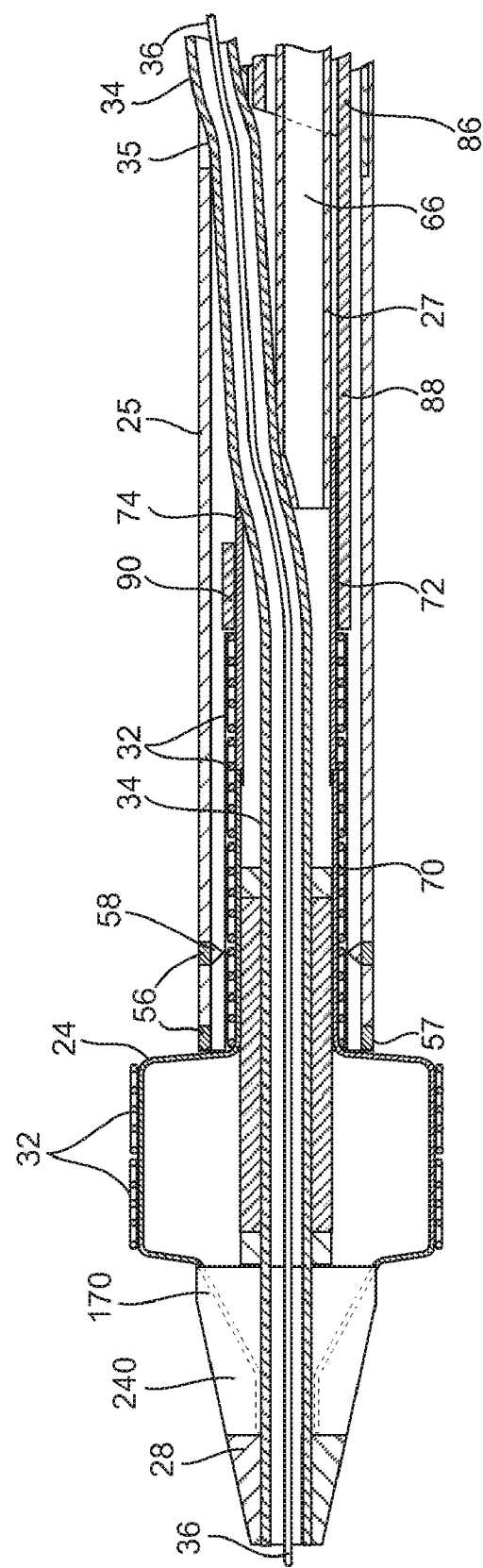
FIG. 17 is a side cross-section of a distal portion of a stent delivery catheter having a stent stop, with expandable member inflated and sheath retracted according to another embodiment of the present invention.

FIG. 17 illustrate another embodiment of a delivery catheter having a stent stop 240 comprising a capsule or sleeve coupled with or integral with the nosecone 28. The stent stop 240 has a hollow interior at its proximal end, which covers the distal taper 170 of expandable member 24. Stent stop 240 thus acts to stop stents 32 at the appropriate location on expandable member 24 as well as to constrain a portion of the expandable member 24 to reduce the size of the distal taper 170.

Figure 18:
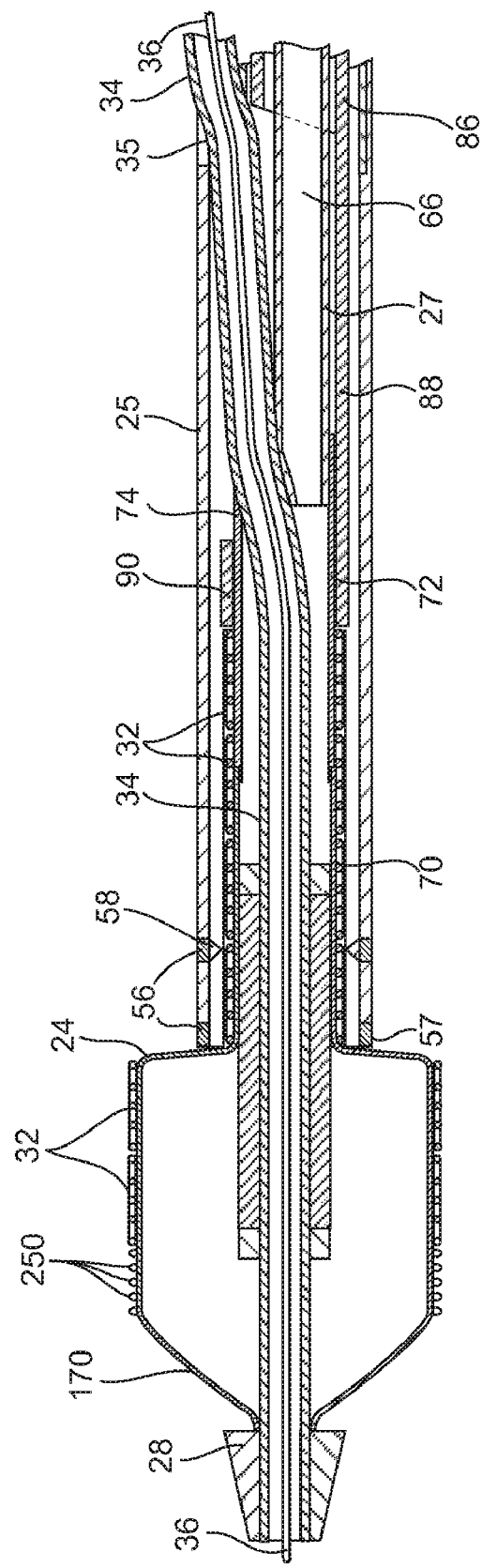
FIG. 18 is a side cross-section of a distal portion of a stent delivery catheter having a stent stop, with expandable member inflated and sheath retracted according to another embodiment of the present invention.

Referring to FIG. 18, another version of a stent stop comprises one or more surface features 250 on the outer surface of the expandable member 24. Such surface features 250 may include, for example, bumps, ridges, spines, ribs, scales, pleats and/or wings. Surface features 250 may be located along the entire length of expandable member 24, or more preferably only near the distal end, just proximal to distal taper 170. In some embodiments, one or more materials may be applied to the outer surface of the expandable member 24 to act as the stent stop. For example, some materials that might be used include Dacron, C-flex, high friction materials, fur, fabric, sponge, wool, gels and/or adhesives. In some embodiments, such as shown in FIG. 18, the surface features 250 may provide a "hard stop," meaning that the stent segments 32 stop by abutting the proximal-most surface feature 250. In other embodiments, the stent segments 32 may begin to slide over the surface features 250 and come to a stop thereon, due to frictional engagement therewith.

Figure 18A:
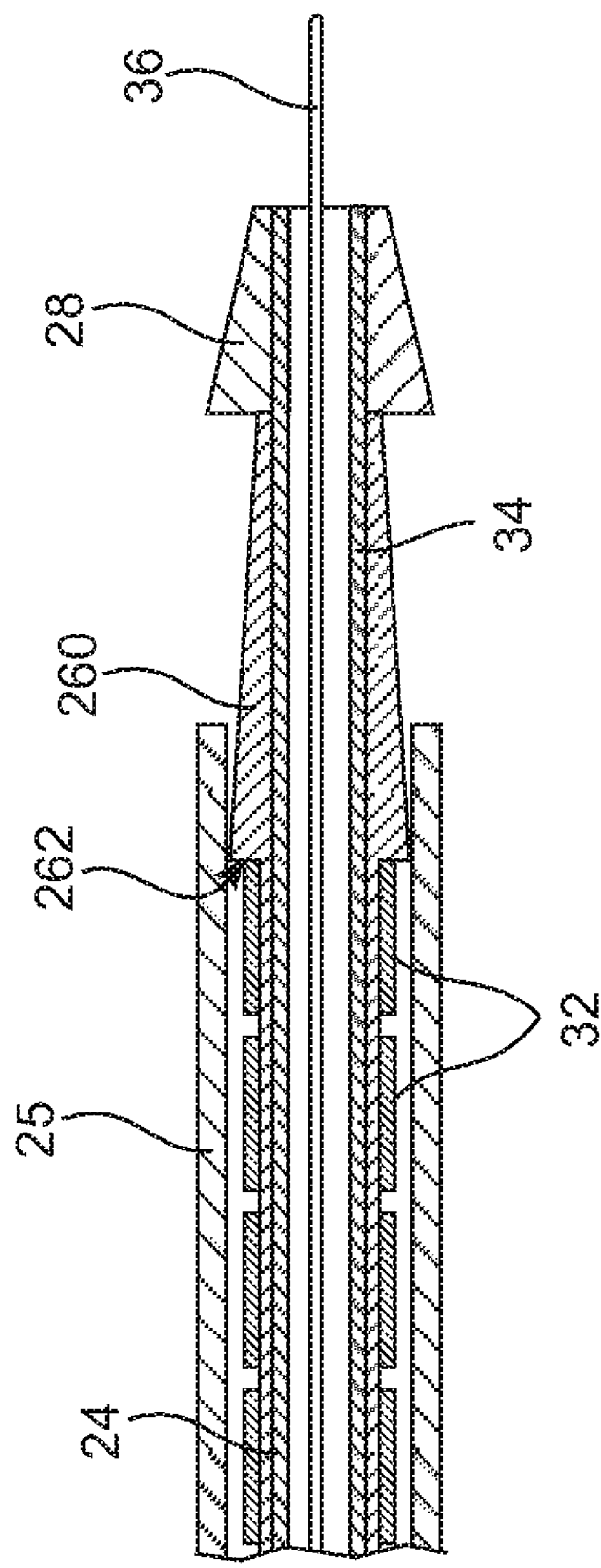
FIG. 18A is a side cross-section of a distal portion of a stent delivery catheter having a stent stop on an expandable member according to another embodiment of the present invention.

Referring to FIG. 18A, a version of a stent stop similar to that just described includes a thickened distal portion 260 of expandable member 24, with thickened distal portion 260 including a proximal end abutment 262 that acts as a stent stop. In various embodiments, thickened portion 260 may have any suitable configuration, shape, diameter or the like, such as the tapered configuration shown in FIG. 18A, a non-tapered, cylindrical configuration or the like. Furthermore, thickened distal portion 260 may be made of any suitable material or combination of materials, such as an elastomeric material. In some embodiments, distal portion 260 is made of the same material as the rest of expandable member 24, while in other embodiments it may be made of one or more different materials. In one embodiment, distal portion 260 is formed by additional dipping of distal portion into elastomer or other material used to form expandable member 24. In one embodiment, as shown, thickened distal portion 260 may have an outer diameter that allows it to be retracted to a position within sheath 25. In alternative embodiments (not shown), proximal end abutment 262 may be sufficiently large or wide that it abuts against the distal end of sheath 25, thus preventing further retraction of distal portion 260 within sheath 25. In some embodiments, an outer surface of distal portion 260, an inner surface of sheath 25, or both may be lubricious in order to facilitated sliding of the two surfaces relative to one another. Such lubricious surfaces may be achieved by use of coatings or by lubricious materials used to make sheath 25, distal portion 260 or both.

In one embodiment (not pictured), a stent stop may not be included on the distal end of the delivery catheter. Instead, following an initial deployment of stent segments, the expandable member is retracted fully into the sheath. This positions the stents at the distal end of the expandable member. The expandable member is then advanced a set distance distally relative to the sheath without pushing on the pusher of the delivery catheter. This positions the stents just proximal to the distal taper on the expandable member. In some embodiments, an actuator on the handle of the device may be configured to automatically advance the expandable member the desired distance.

Figure 19:
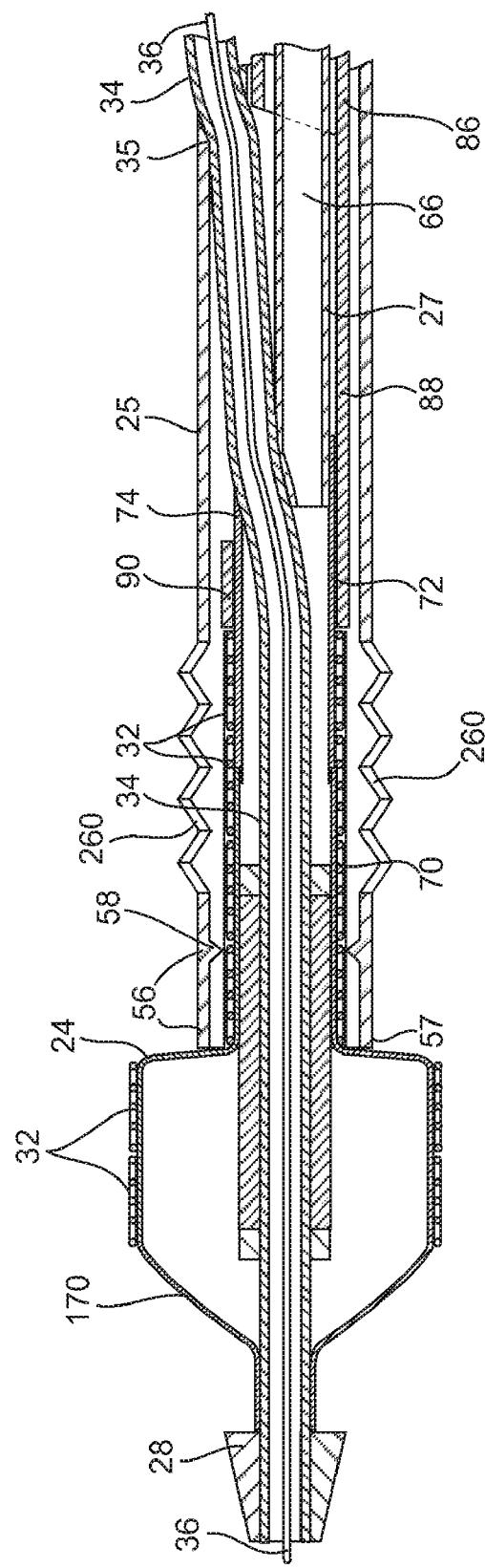
FIG. 19 is a side cross-section of a distal portion of a stent delivery catheter having a stent stop, with expandable member inflated and sheath retracted according to another embodiment of the present invention.

A variation of the embodiment just described is illustrated in FIG. 19. Again, this embodiment does not include a stent stop. In this embodiment the sheath 25 includes a spring section 260 near its distal end (or elsewhere along its length in other embodiments). When the expandable member 24 is retracted into the sheath 25, the distal end of the sheath 25 engages the nose cone 28. The expandable member 24 may be retracted to compress the spring section 260, and the expandable member may subsequently be released to allow the spring section 260 to recoil, thus advancing the expandable member 24 by a preset distance relative to the sheath 25 and the stent segments 32. This positions stent segments 32 with sufficient spacing from the distal end of the expandable member 24 to allow for the distal taper 170.

While the foregoing description of the invention is directed to a stent delivery catheter for deploying stents into vascular lumens to maintain patency, various other types of wire-guided catheters also may embody the principles of the invention. For example, balloon catheters for angioplasty and other purposes, particularly those having a slidable external sheath surrounding the balloon, may be constructed in accordance with the invention. Other types of catheters for deployment of prosthetic devices such as embolic coils, stent grafts, aneurism repair devices, annuloplasty rings, heart valves, anastomosis devices, staples or clips, as well as ultrasound and angiography catheters, electrophysiological mapping and ablation catheters, and other devices may also utilize the principles of the invention.

Although the above is complete description of the preferred embodiments of the invention, various alternatives, additions, modifications and improvements may be made without departing from the scope thereof, which is defined by the claims.

What is claimed is:

1. An apparatus for delivering a prosthesis into a target vessel of a patient's body, said apparatus comprising:
   a flexible catheter shaft having a distal end disposed in the target vessel and a proximal end disposed outside the body;
   an expandable member disposed near the distal end of the catheter shaft, the expandable member being movable from a contracted configuration to an expanded configuration;
   a tubular prosthesis axially positionable over and in contact with the expandable member, the prosthesis having an unexpanded configuration and being radially expandable to a deployed configuration for deployment in the target vessel, wherein the unexpanded tubular prosthesis is slidably disposed on the catheter shaft near the distal end of the catheter, and wherein the unexpanded prosthesis is selectively movable in an axial direction over the expandable member with a mechanism controllable from the proximal end of the catheter shaft; and
   a stop member axially fixed relative to the catheter shaft near the distal end thereof, wherein the stop member inhibits axial displacement of the prosthesis distally of a deployment position along the expandable member when the prosthesis is in the unexpanded configuration, and wherein the prosthesis is expandable to the deployed configuration by the expandable member when disposed at the deployment position.

2. The apparatus of claim 1, wherein the stop member is attached to the catheter shaft.

3. The apparatus of claim 2, wherein the stop member comprises an annular structure around the catheter shaft.

4. The apparatus of claim 1, wherein the stop member is disposed outside of the expandable member.

5. The apparatus of claim 1, wherein the expandable member is disposed over the stop member.

6. The apparatus of claim 5, wherein the expandable member is attached to the stop member.

7. The apparatus of claim 1, wherein the stop member is disposed on a surface of expandable member.

8. The apparatus of claim 7, wherein the stop member comprises at least one surface feature on the expandable member configured to engage the prosthesis.

9. The apparatus of claim 1, further comprising a nosecone attached to the distal end of the catheter shaft, the stop member being attached to the nosecone.

10. The apparatus of claim 1, wherein the expandable member comprises a working portion having a generally constant outer diameter in the expanded configuration, and wherein the stop member is positioned to inhibit displacement of the tubular prosthesis distally of the working portion.

11. The apparatus of claim 10, wherein the expandable member further comprises a distal leg coupled to the catheter shaft and a distal taper which connects the working portion to the distal leg, the distal taper having, in the expanded configuration, a diameter which decreases between the working portion and the distal leg, and wherein the stop member is positioned to keep the prosthesis proximal to the distal taper.

12. The apparatus of claim 1, wherein the stop member imparts friction to an inner surface of the prosthesis.

13. The apparatus of claim 1, wherein the stop member has an abutment that engages a distal end of the prosthesis.

14. The apparatus of claim 1, wherein the mechanism comprises a pusher slidably coupled to the catheter shaft and adapted to move the prosthesis relative to the expandable member.

15. The apparatus of claim 1, wherein the mechanism comprises a retractable sheath, the prosthesis comprises at least one stent segment, and the sheath comprises a distalmost portion reinforced to resist radial expansion so as to prevent expansion of the prosthesis while allowing at least a distal portion of the expandable member to be expanded without expanding the prosthesis.

16. The apparatus of claim 15, wherein the length of the distal portion of the expandable member is selectively changeable from the proximal end of the catheter shaft.

17. The apparatus of claim 15, wherein the mechanism is operably coupled to the prosthesis so as to move the prosthesis onto the distal portion of the expandable member.

18. The apparatus of claim 17, wherein the mechanism for moving the prosthesis onto the expandable member comprises a pusher slidably coupled to the catheter shaft.

19. The apparatus of claim 15, wherein the mechanism is coupleable with the prosthesis so as to move the prosthesis off the distal portion of the expandable member.

20. The apparatus of claim 1, wherein the mechanism for moving the prosthesis off the distal portion of the expandable member comprises a retractable sheath slidably coupled to the catheter shaft and covering the expandable member and prosthesis.

21. The apparatus of claim 20, wherein the sheath has a separation member that engages the prosthesis such that the prosthesis is retractable in conjunction with the sheath.

22. The apparatus of claim 1, further comprising an additional quantity of tubular prostheses positionable over and in contact with the expandable member, each of the additional quantity of prostheses having an unexpanded configuration and being radially expandable to a deployed configuration for deployment in the target vessel.

23. The apparatus of claim 22, wherein at least a first prosthesis is positionable on the expandable member for expansion therewith while at least a second prosthesis is maintained in the unexpanded configuration.

24. The apparatus of claim 23, further comprising a mechanism controllable from the proximal end of the catheter shaft for selectively changing the number of prostheses that are positioned for expansion by the expandable member.

25. The apparatus of claim 24, wherein the mechanism for selectively changing the number of prostheses comprises a retractable sheath slidably coupled to the catheter shaft and covering the prostheses and expandable member.

26. The apparatus of claim 25, wherein the sheath is adapted to retract a selectable number of the prostheses proximally relative to the expandable member.

27. The apparatus of claim 25, wherein the sheath is adapted to expose a selectable number of the prostheses distally of the sheath for expansion with the expandable member.

28. The apparatus of claim 25, wherein the sheath is adapted to constrain expansion of a proximal portion of the expandable member and the prostheses disposed thereon which are covered by the sheath.

29. The apparatus of claim 25, further comprising a separation member on the sheath adapted to engage at least one prosthesis such that it is retractable in conjunction with the sheath.

30. The apparatus of claim 24, wherein the mechanism for selectively changing the number of prostheses comprises a pusher slidably coupled to the catheter shaft and adapted to apply a distally directed force to the prostheses.

31. An apparatus for delivering a prosthesis into a target vessel of a patient's body, said apparatus comprising:
- a flexible catheter shaft having a distal end disposed in the target vessel and a proximal end disposed outside the body;
- an expandable member disposed at the distal end of the catheter, the expandable member being movable from a contracted configuration to an expanded configuration;
- a tubular prosthesis axially positionable over and in contact with the expandable member, the prosthesis having an unexpanded configuration and being radially expandable to a deployed configuration for deployment in the target vessel, wherein the unexpanded tubular prosthesis is slidably disposed on the catheter shaft near the distal end of the catheter shaft, and wherein the unexpanded prosthesis is selectively movable in an axial direction over the expandable member;
- a mechanism controllable from the proximal end of the catheter shaft for selectively moving the unexpanded prosthesis in an axial direction over the expandable member; and
- a stop member axially fixed relative to the catheter shaft near the distal end thereof, wherein the stop member inhibits axial displacement of the prosthesis distally of a deployment position along the expandable member when the prosthesis is in the unexpanded configuration and wherein the prosthesis is expandable to the deployed configuration by the expandable member when disposed at the deployment position; and wherein the prosthesis is expandable to the deployed configuration by the expandable member when disposed at the deployment position.

32. The apparatus of claim 31, wherein the stop member is attached to the catheter shaft.

33. The apparatus of claim 32, wherein the stop member comprises an annular structure around the catheter shaft.

34. The apparatus of claim 31, wherein the stop member is disposed outside of the expandable member.

35. The apparatus of claim 31, wherein the expandable member is disposed over the stop member.

36. The apparatus of claim 35, wherein the expandable member is attached to the stop member.

37. The apparatus of claim 31, wherein the stop member is disposed on a surface of the expandable member.

38. The apparatus of claim 37, wherein the stop member comprises at least one surface feature on the expandable member configured to engage the prosthesis.

39. The apparatus of claim 31, further comprising a nosecone attached to the distal end of the catheter shaft, the stop member being attached to the nosecone.

40. The apparatus of claim 31, wherein the expandable member comprises a working portion having a generally constant outer diameter in the expanded configuration, and wherein the stop member is positioned to inhibit displacement of the tubular prosthesis distally of the working portion.

41. The apparatus of claim 40, wherein the expandable member further comprises a distal leg coupled to the catheter shaft and a distal taper which connects the working portion to the distal leg, the distal taper having, in the expanded configuration, a diameter which decreases between the working portion and the distal leg, and wherein the stop member is positioned to keep the prosthesis proximal to the distal taper.

42. The apparatus of claim 31, wherein the stop member imparts friction to an inner surface of the prosthesis.

43. The apparatus of claim 31, wherein the stop member has an abutment that engages a distal end of the prosthesis.

44. The apparatus of claim 31, wherein the mechanism comprises a pusher slidably coupled to the catheter shaft and adapted to move the prosthesis relative to the expandable member.

45. The apparatus of claim 31, wherein the length of the distal portion of the expandable member is selectively changeable from the proximal end of the catheter shaft.

46. The apparatus of claim 31, wherein the mechanism is coupleable with the prosthesis so as to move the prosthesis onto the distal portion of the expandable member.

47. The apparatus of claim 46, wherein the mechanism for moving the prosthesis onto the expandable member comprises a pusher slidably coupled to the catheter shaft.

48. The apparatus of claim 31, wherein the mechanism is coupleable with the prosthesis so as to move the prosthesis off the distal portion of the expandable member.

49. The apparatus of claim 48, wherein the mechanism for moving the prosthesis off the distal portion of the expandable member comprises a retractable sheath slidably coupled to the catheter shaft and covering the expandable member and prosthesis.

50. The apparatus of claim 49, wherein the sheath has a separation member that engages the prosthesis such that the prosthesis is retractable in conjunction with the sheath.

51. The apparatus of claim 31, further comprising an additional quantity of tubular prostheses positionable over and in contact with the expandable member, each of the additional quantity of prostheses having an unexpanded configuration and being radially expandable to a deployed configuration for deployment in the target vessel.

52. The apparatus of claim 51, wherein at least a first prosthesis is positionable on the expandable member for expansion therewith while at least a second prosthesis is maintained in the unexpanded configuration.

53. The apparatus of claim 52, further comprising a mechanism controllable from the proximal end of the catheter shaft for selectively changing the number of prostheses that are positioned for expansion by the expandable member.

54. The apparatus of claim 53, wherein the mechanism for selectively changing the number of prostheses comprises a retractable sheath slidably coupled to the catheter shaft and covering the prostheses and expandable member.

55. The apparatus of claim 54, wherein the sheath is adapted to retract a selectable number of the prostheses proximally relative to the expandable member.

56. The apparatus of claim 54, wherein the sheath is adapted to expose a selectable number of the prostheses distally of the sheath for expansion with the expandable member.

57. The apparatus of claim 54, wherein the sheath comprises a reinforced distal-most portion adapted to resist radial expansion so as to constrain expansion of a proximal portion of the expandable member and the prostheses disposed thereon which are covered by the sheath.

58. The apparatus of claim 54, further comprising a separation member on the sheath adapted to engage at least one prosthesis such that it is retractable in conjunction with the sheath.

59. The apparatus of claim 53, wherein the mechanism for selectively changing the number of prostheses comprises a pusher slidably coupled to the catheter shaft and adapted to apply a distally directed force to the prostheses.

* * * * *